US012667327B2

(12) United States Patent
Miyachi

(10) Patent No.: US 12,667,327 B2
(45) Date of Patent: Jun. 30, 2026

(54) MEDICAL IMAGE ACQUISITION GUIDANCE DEVICE, MEDICAL IMAGE ACQUISITION GUIDANCE SYSTEM, AND PROGRAM

(71) Applicant: FUJIFILM Corporation, Tokyo (JP)

(72) Inventor: Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/066,085

(22) Filed: Feb. 27, 2025

(65) Prior Publication Data

US 2025/0295375 A1　　Sep. 25, 2025

(30) Foreign Application Priority Data

Mar. 25, 2024　(JP) ................................. 2024-047954

(51) Int. Cl.
*A61B 8/08*　　　(2006.01)
*A61B 6/00*　　　(2006.01)
*A61B 6/50*　　　(2024.01)
*A61B 8/00*　　　(2006.01)

(52) U.S. Cl.
CPC ............ *A61B 8/0825* (2013.01); *A61B 6/488* (2013.01); *A61B 6/502* (2013.01); *A61B 8/403* (2013.01); *A61B 8/463* (2013.01); *A61B 8/5261* (2013.01)

(58) Field of Classification Search
CPC ....... A61B 8/0825; A61B 6/488; A61B 6/502; A61B 8/403; A61B 8/463; A61B 8/5261; A61B 6/025; A61B 6/0414; A61B 6/4417; A61B 6/462; A61B 8/4416; A61B 6/5247; A61B 8/085; A61B 8/4245; A61B 8/54
See application file for complete search history.

(56) References Cited

U.S. PATENT DOCUMENTS

2009/0088637 A1　　4/2009　Mikami
2023/0103969 A1　　4/2023　St. Pierre et al.

FOREIGN PATENT DOCUMENTS

EP　　　3 692 921 A1　　8/2020
EP　　　4 331 494 A1　　3/2024
JP　　　2009-082402 A　　4/2009
WO　　2020/069031 A1　　4/2020

OTHER PUBLICATIONS

Extended European Search Report issued in EP 25 16 3931.6-1122 by the European Patent Office on Jul. 1, 2025, which is related to U.S. Appl. No. 19/066,085.

*Primary Examiner* — Joel Lamprecht
(74) *Attorney, Agent, or Firm* — Studebaker Brackett PLLC

(57) ABSTRACT

A console as a medical image acquisition guidance device includes a projection processing unit configured to, in a case in which a radiation image and an ultrasound image of a breast in a state of being compressed by a compression member are captured, perform processing of projecting a guide image for guiding at least one of a scanning region or a scanning direction of an ultrasound probe used for capturing the ultrasound image onto a side of the compression member opposite to a compression side of the breast according to an effective width, which is a region in which transmission and reception of an ultrasonic wave are possible, of the ultrasound probe, in capturing the ultrasound image.

11 Claims, 14 Drawing Sheets

FIG. 6

PROBE INFORMATION DATABASE

| PROBE ID | PROBE INFORMATION | |
|---|---|---|
| | PROBE WIDTH (mm) | HOUSING WIDTH (mm) |
| P001 | 50 | 52 |
| P002 | 35 | 37 |
| ⋮ | ⋮ | ⋮ |

FIG. 7

REGISTRATION INFORMATION DATABASE

| RADIATION IMAGE | REGISTRATION INFORMATION | | | |
|---|---|---|---|---|
| | PROBE ID | ULTRASOUND IMAGE | SCANNING REGION | SCANNING DIRECTION |
| (RADIATION IMAGE A) | P001 | (ULTRASOUND IMAGE a1) | (SCANNING REGION ar1) | (SCANNING DIRECTION R) |
| | | (ULTRASOUND IMAGE a2) | (SCANNING REGION ar2) | (SCANNING DIRECTION R) |
| | | (ULTRASOUND IMAGE a3) | (SCANNING REGION ar3) | (SCANNING DIRECTION R) |
| | | (ULTRASOUND IMAGE a4) | (SCANNING REGION ar4) | (SCANNING DIRECTION R) |
| (RADIATION IMAGE B) | P002 | (ULTRASOUND IMAGE b1) | (SCANNING REGION br1) | (SCANNING DIRECTION R) |
| | | (ULTRASOUND IMAGE b2) | (SCANNING REGION br2) | (SCANNING DIRECTION L) |
| | | (ULTRASOUND IMAGE b3) | (SCANNING REGION br3) | (SCANNING DIRECTION R) |
| | | (ULTRASOUND IMAGE b4) | (SCANNING REGION br4) | (SCANNING DIRECTION L) |
| | | (ULTRASOUND IMAGE b5) | (SCANNING REGION br5) | (SCANNING DIRECTION R) |
| ⋮ | ⋮ | ⋮ | ⋮ | ⋮ |

FIG. 8

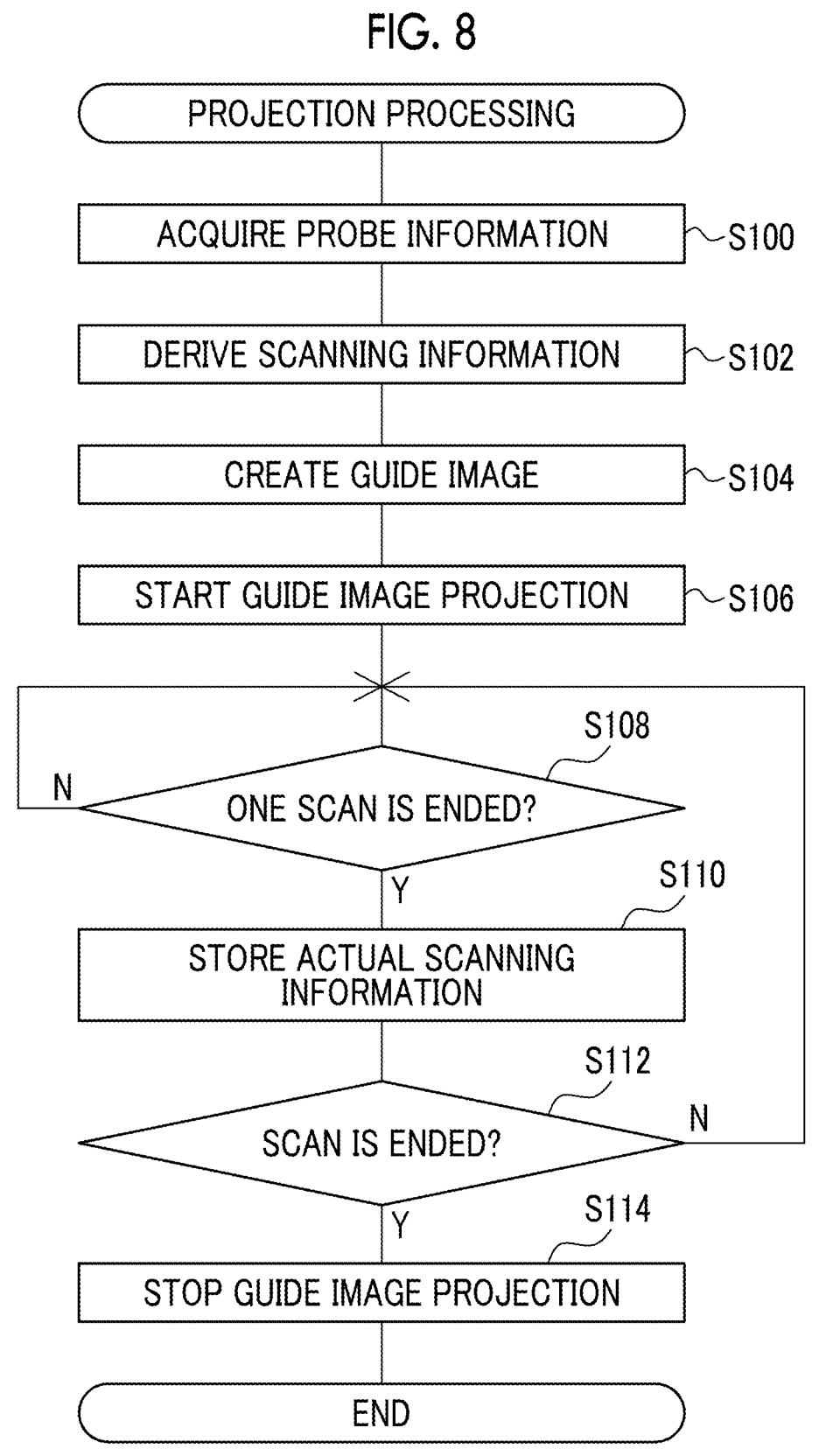

PROJECTION PROCESSING

ACQUIRE PROBE INFORMATION — S100

DERIVE SCANNING INFORMATION — S102

CREATE GUIDE IMAGE — S104

START GUIDE IMAGE PROJECTION — S106

S108

ONE SCAN IS ENDED? — N

Y

STORE ACTUAL SCANNING INFORMATION — S110

S112

SCAN IS ENDED? — N

Y

STOP GUIDE IMAGE PROJECTION — S114

END

FIG. 15

MEDICAL IMAGE ACQUISITION GUIDANCE DEVICE, MEDICAL IMAGE ACQUISITION GUIDANCE SYSTEM, AND PROGRAM

CROSS-REFERENCE TO RELATED APPLICATIONS

This application claims priority under 35 USC 119 from Japanese Patent Application No. 2024-047954 filed on Mar. 25, 2024, the disclosure of which is incorporated by reference herein.

BACKGROUND

1. Technical Field

The present disclosure relates to a medical image acquisition guidance device, a medical image acquisition guidance system, and a program.

2. Related Art

In a radiation image obtained by mammography, both a lesion (tumor, calcification, or the like) due to breast cancer and a mammary gland are displayed in white. Therefore, in a case of a breast having a high mammary gland density, a lesion due to breast cancer is hidden in a mammary gland region and is difficult to find. On the other hand, an ultrasound image obtained through an ultrasound examination is suitable for imaging a breast having a high mammary gland density, but the mammary gland density varies from person to person.

Therefore, in the related art, the following technique has been used as a technique in which an examination using mammography and an ultrasound result are used in combination.

JP2009-82402A discloses a medical image diagnosis system that aims to visually recognize a radiation image and an ultrasound image in association with each other in a medical image diagnosis system that performs diagnosis of a mammary gland and a breast using radiation and ultrasound in combination.

This medical image diagnosis system includes: a medical imaging apparatus that irradiates a subject with radiation to acquire a radiation image of the subject projected onto a projection surface, that transmits an ultrasonic wave toward the subject and receives an ultrasound echo reflected by the subject to acquire an ultrasound slice image of the subject along a slice plane substantially orthogonal to the projection surface, and that generates first image data representing a plurality of the ultrasound slice images along a plurality of the slice planes, second image data representing at least one radiation image, and position data representing positions of the plurality of slice planes on the projection surface; a medical image storage device that stores the first image data, the second image data, and the position data generated by the medical imaging apparatus in association with each other; and a medical image display device that displays at least one ultrasound slice image along at least one slice plane based on the first image data read out from the medical image storage device, and that displays at least one radiation image on which a marker indicating the position of the at least one slice plane on the projection surface is represented based on the second image data and the position data read out from the medical image storage device.

SUMMARY

Incidentally, in a case in which the radiation image and the ultrasound image are captured in a state where the breast is compressed using a compression member, it is necessary to make a time for which the breast is compressed by the compression member as short as possible, taking into consideration a burden on the subject.

However, the technique disclosed in JP2009-82402A has a problem in that scanning is performed manually using an ultrasound probe, which takes a relatively long time.

In general, in a case of manually capturing an ultrasound image using the ultrasound probe, an ultrasound image acquired by one scanning operation is limited to an image of a partial region of the entire breast, so that it is necessary to perform scanning a plurality of times.

In particular, in an examination in which a radiation image and an ultrasound image are used in combination, there is a need to read the images as a whole by superimposing the images, and in this case, an ultrasound image of the entire breast is required. However, in a case in which the ultrasound image is captured a plurality of times for this purpose, a part of an imaging region may be omitted, and in this case, it is necessary to perform imaging again on the omitted part.

The present disclosure has been made in view of the above circumstances, and an object of the present disclosure is to provide a medical image acquisition guidance device, a medical image acquisition guidance system, and a program capable of performing ultrasonography in a state where a breast is compressed by a compression member in a shorter time than in the related art.

In order to achieve the above object, a first aspect of the present disclosure provides a medical image acquisition guidance device comprising: at least one processor, in which the processor is configured to, in a case in which a radiation image and an ultrasound image of a breast in a state of being compressed by a compression member are captured, perform processing of projecting a guide image for guiding at least one of a scanning region or a scanning direction of an ultrasound probe used for capturing the ultrasound image onto a side of the compression member opposite to a compression side of the breast according to an effective width, which is a region in which transmission and reception of an ultrasonic wave are possible, of the ultrasound probe, in capturing the ultrasound image.

A second aspect of the present disclosure provides the medical image acquisition guidance device according to the first aspect, in which the processor is configured to further perform processing of storing the ultrasound image obtained by scanning using the ultrasound probe and at least one of the scanning region or the scanning direction in the scanning for obtaining the ultrasound image in association with each other.

A third aspect of the present disclosure provides the medical image acquisition guidance device according to the second aspect, in which the processor is configured to specify at least one of an actual scanning region or an actual scanning direction using a detection result of a position sensor that detects a position of the ultrasound probe.

A fourth aspect of the present disclosure provides the medical image acquisition guidance device according to the second or third aspect, in which the processor is configured to, in a case in which the ultrasound image is stored in association with the scanning region, further perform first display processing of displaying the radiation image corresponding to the ultrasound image together with a scanning region image which is an image showing the scanning region, and, in a case in which the scanning region shown in the scanning region image displayed by the first display processing is designated by a user, further perform second display processing of displaying the ultrasound image corresponding to the scanning region.

A fifth aspect of the present disclosure provides the medical image acquisition guidance device according to the first or second aspect, in which the processor is configured to, in a case in which scanning using the ultrasound probe is performed a plurality of times to capture a single ultrasound image, decide the scanning regions corresponding to scans adjacent to each other such that the adjacent regions overlap each other within a predetermined range.

A sixth aspect of the present disclosure provides the medical image acquisition guidance device according to the first or second aspect, in which the guide image is an image including at least one of a line, a figure, a mark, or a character.

A seventh aspect of the present disclosure provides the medical image acquisition guidance device according to the first or second aspect, in which the processor is configured to project the guide image onto the side of the compression member opposite to the compression side of the breast and onto a region excluding the scanning region of the ultrasound probe.

An eighth aspect of the present disclosure provides the medical image acquisition guidance device according to the first or second aspect, in which the processor is configured to decide the scanning region using at least one of a width of a housing of the ultrasound probe, the effective width of the ultrasound probe, a width of the compression member, or an acquisition region of an image showing the breast in the radiation image.

A ninth aspect of the present disclosure provides the medical image acquisition guidance device according to the first or second aspect, in which the processor is configured to acquire the effective width at any one of a timing at which the medical image acquisition guidance device is powered on, a timing at which the ultrasound probe is attached, or a timing at which a preset for acquiring an image showing the breast is selected.

In addition, in order to achieve the above object, a tenth aspect of the present disclosure provides a medical image acquisition guidance system comprising: the medical image acquisition guidance device according to the present disclosure; and a display unit that displays the radiation image and the ultrasound image acquired in accordance with the processing performed by the medical image acquisition guidance device.

In addition, in order to achieve the above object, an eleventh aspect of the present disclosure provides a program causing a computer to execute a process comprising: performing, in a case in which a radiation image and an ultrasound image of a breast in a state of being compressed by a compression member are captured, processing of projecting a guide image for guiding at least one of a scanning region or a scanning direction of an ultrasound probe used for capturing the ultrasound image onto a side of the compression member opposite to a compression side of the breast according to an effective width, which is a region in which transmission and reception of an ultrasonic wave are possible, of the ultrasound probe, in capturing the ultrasound image.

According to the present disclosure, it is possible to perform ultrasonography in a state where a breast is compressed by a compression member in a shorter time than in the related art.

BRIEF DESCRIPTION OF THE DRAWINGS

Exemplary embodiments of the technology of the disclosure will be described in detail based on the following figures, wherein:

FIG. 6 is a schematic diagram showing an example of a configuration of a probe information database according to the embodiment;

FIG. 7 is a schematic diagram showing an example of a configuration of a registration information database according to the embodiment;

FIG. 8 is a flowchart showing an example of projection processing according to the embodiment;

FIG. 15 is a diagram showing an example of a display state of a body mark according to the embodiment;

DETAILED DESCRIPTION

Hereinafter, an embodiment of the present disclosure will be described with reference to the drawings.

Figure 1:
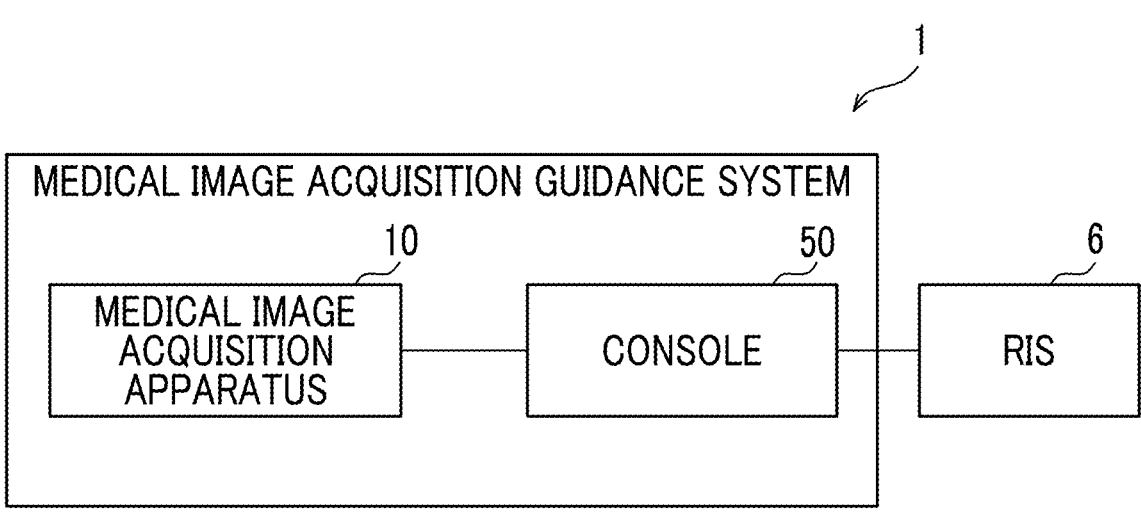
FIG. 1 is a diagram showing an example of a schematic configuration of a medical image acquisition guidance system according to an embodiment.

First, a configuration of a medical image acquisition guidance system 1 to which a technique of the present disclosure is applied will be described with reference to FIG. 1. FIG. 1 is a diagram showing an example of a schematic configuration of the medical image acquisition guidance system 1 according to the present embodiment.

As shown in FIG. 1, the medical image acquisition guidance system 1 comprises a medical image acquisition apparatus 10 and a console 50. The medical image acquisition apparatus 10 and the console 50, and the console 50 and an external radiology information system (RIS) 6 are configured to be connected to each other via a wired or wireless network. The console 50 corresponds to a medical image acquisition guidance device in the technology of the present disclosure.

In the medical image acquisition guidance system 1 according to the present embodiment, the console 50 acquires an imaging order or the like from the RIS 6, and controls the medical image acquisition apparatus 10 in accordance with the imaging order, an instruction from a user, and the like. The medical image acquisition apparatus 10 captures a radiation image by irradiating a breast put into a compressed state between an imaging table 16 and a compression member 40, both of which will be described below, with radiation R. In addition, the medical image acquisition apparatus 10 captures an ultrasound image of the breast put into the compressed state by the compression member 40.

Figure 2:
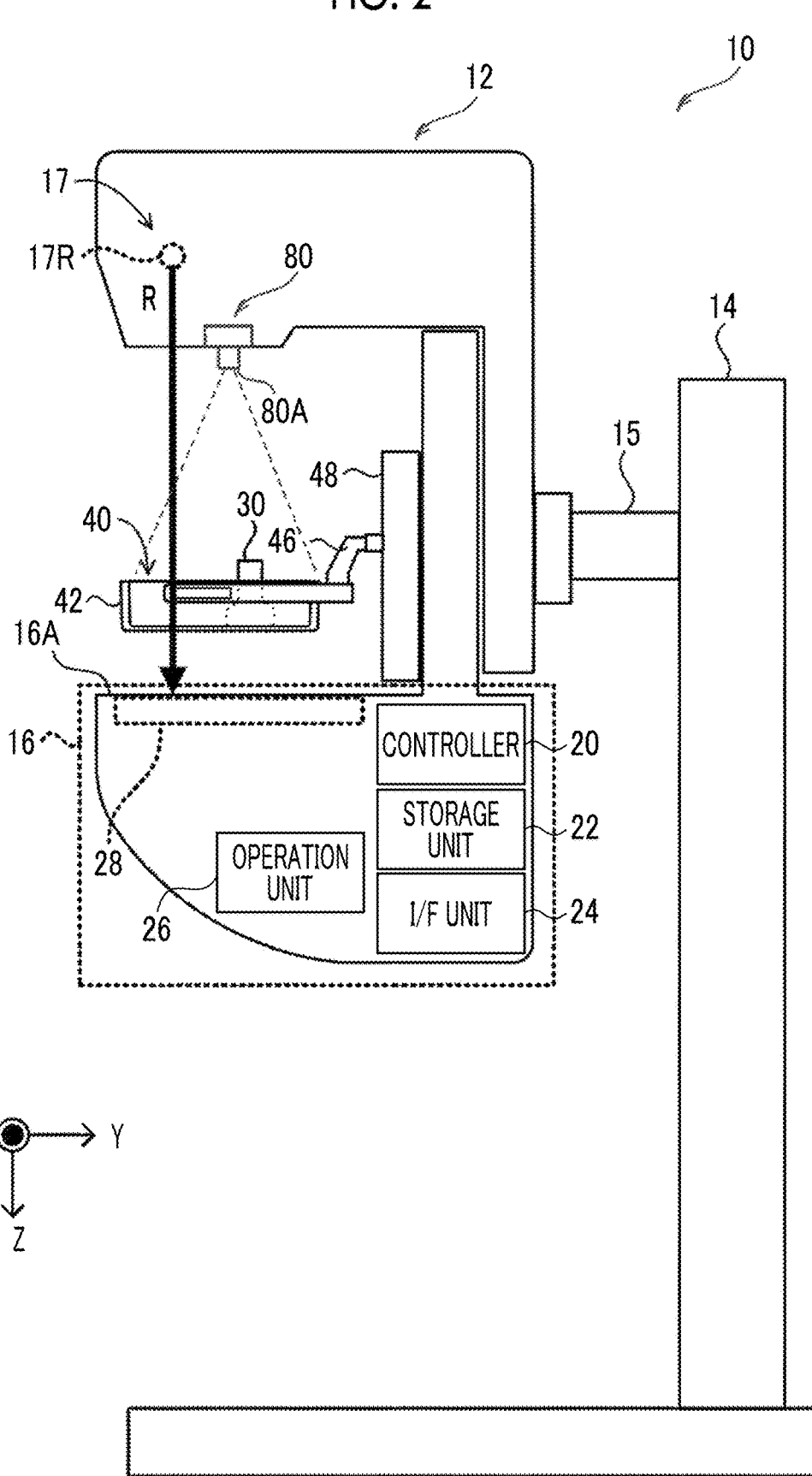
FIG. 2 is a side view showing an example of an appearance of a medical image acquisition apparatus according to the embodiment.

Next, a schematic configuration of the medical image acquisition apparatus 10 according to the present embodiment will be described with reference to FIG. 2. FIG. 2 is a side view showing an example of an appearance of the medical image acquisition apparatus 10 according to the present embodiment, and is a view of the medical image acquisition apparatus 10 as viewed from a right side of a subject. As shown in FIG. 2, the medical image acquisition apparatus 10 comprises a radiation source 17R, a radiation detector 28, an imaging table 16 disposed between the radiation source 17R and the radiation detector 28, and a compression member 40 that compresses the breast between the compression member 40 and the imaging table 16. In the medical image acquisition apparatus 10, a user, such as a doctor or a technician, positions the breast of the subject on an imaging surface 16A of the imaging table 16.

The medical image acquisition apparatus 10 comprises an arm part 12, a base 14, and a shaft part 15. The arm part 12 is held by the base 14 so as to be movable in an up-down direction (Z direction). The shaft part 15 connects the arm part 12 to the base 14. The arm part 12 is rotatable relative to the base 14, using the shaft part 15 as a rotation axis. In addition, the arm part 12 may be configured such that an upper part comprising a radiation emitting unit 17 and a lower part comprising the imaging table 16 are separately rotatable relative to the base 14, using the shaft part 15 as the rotation axis.

The arm part 12 comprises the radiation emitting unit 17 and the imaging table 16. The radiation emitting unit 17 comprises the radiation source 17R, and is configured to change an irradiation field of radiation (for example, X-rays) emitted from the radiation source 17R. The change of the irradiation field may be performed, for example, by the user operating an operation unit 26 or by a controller 20 in accordance with a type of the attached compression member 40.

The imaging table 16 comprises the controller 20, a storage unit 22, an interface (I/F) unit 24, the operation unit 26, and the radiation detector 28. The controller 20 controls an overall operation of the medical image acquisition apparatus 10 under the control of the console 50. The controller 20 comprises a central processing unit (CPU), a read only memory (ROM), a random access memory (RAM), and the like (not shown). The ROM stores in advance various programs various programs, including a program for controlling the generation of the radiation image and the ultrasound image, which are executed by the CPU. The RAM transitorily stores various data.

Data of the radiation image and the ultrasound image, various types of other information, and the like are stored in the storage unit 22. The storage unit 22 is implemented by, for example, a storage medium such as a hard disk drive (HDD), a solid state drive (SSD), and a flash memory.

The I/F unit 24 performs communication of various types of information with the console 50 through wired communication or wireless communication. Specifically, the I/F unit 24 receives information related to the control of the medical image acquisition apparatus 10 from the console 50. In addition, the I/F unit 24 transmits the data of the radiation image and the ultrasound image to the console 50.

The operation unit 26 is a part that is provided on the imaging table 16 or the like and that is operable by the user with a hand, a foot, or the like, and is, for example, a switch, a button, or a touch panel.

The radiation detector 28 is disposed inside the imaging table 16, detects the radiation R transmitted through the breast and the imaging table 16, generates a radiation image based on the detected radiation R, and outputs image data representing the generated radiation image. A type of the radiation detector 28 is not particularly limited and may be, for example, an indirect conversion type radiation detector that converts the radiation R into light and converts the converted light into a charge, or may be a direct conversion type radiation detector that directly converts the radiation R into a charge.

A compression unit 48 is connected to the arm part 12. A support part 46 that supports the compression member 40 is attachably and detachably attached to the compression unit 48. The support part 46 (compression member 40) is moved in the up-down direction (Z direction) by a driving unit (not shown) provided in the compression unit 48.

Figure 3:
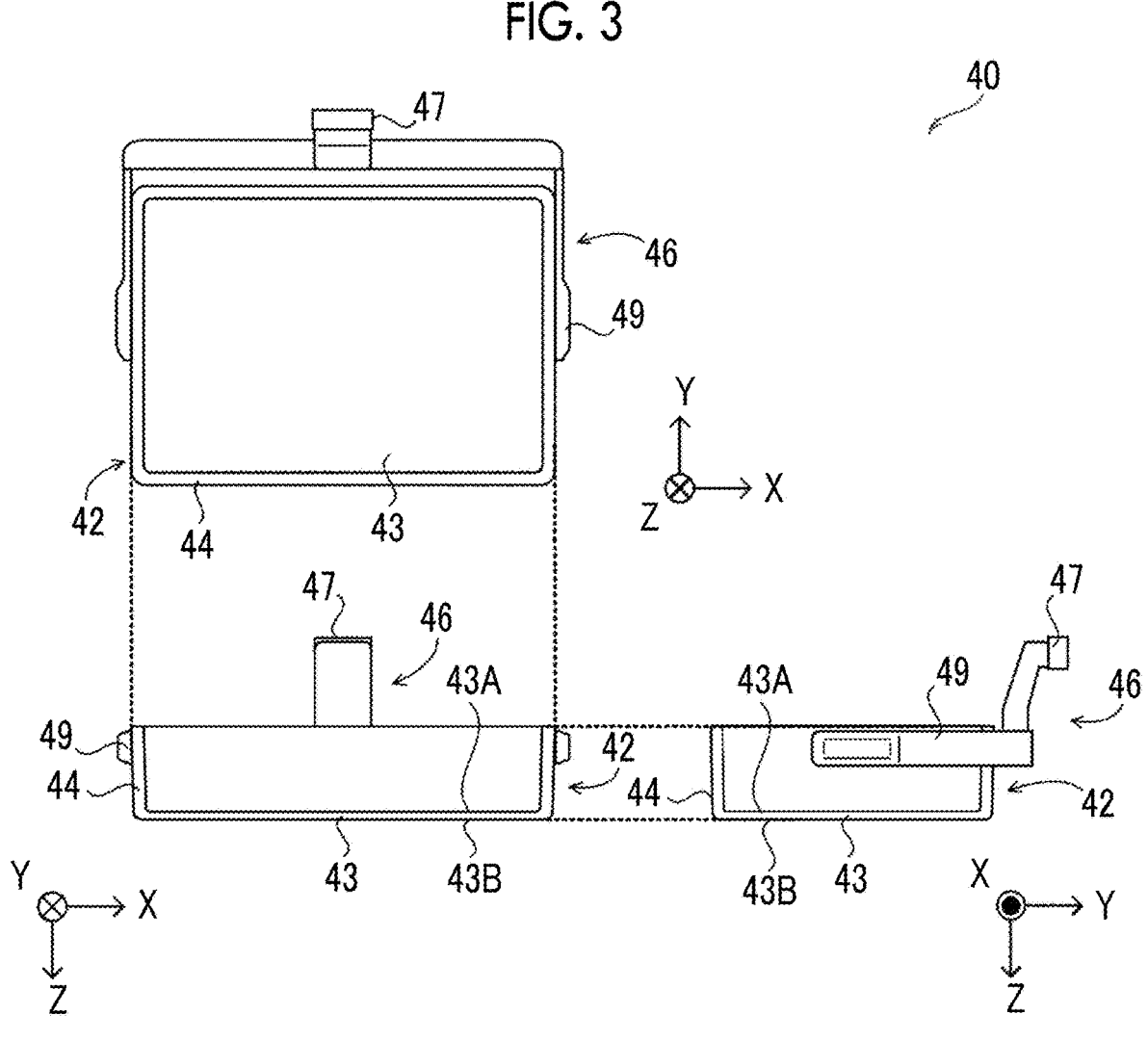
FIG. 3 is a three-plane view showing an example of a schematic configuration of a compression member according to the embodiment.

The compression member 40 is disposed between the radiation source 17R and the imaging table 16 and sandwiches the breast between the compression member 40 and the imaging table 16 to put the breast into a compressed state. FIG. 3 shows a three-plane diagram of an example of the compression member 40. The three-plane diagram of FIG. 3 includes a top view of the compression member 40 as viewed from above (radiation emitting unit 17 side), a side view thereof as viewed from a subject side, and a side view thereof as viewed from a right side of the subject. As shown in FIG. 3, the compression member 40 includes a compression part 42 and the support part 46.

The support part 46 includes an attachment portion 47 and an arm 49. The attachment portion 47 attaches the compression member 40 to the medical image acquisition apparatus 10, specifically, the driving unit of the compression unit 48. The arm 49 supports the compression part 42.

The compression part 42 includes a bottom portion 43 formed to be substantially flat and surrounded by a wall portion 44 having a substantially uniform height and has a recessed cross-sectional shape. The compression part 42 is preferably formed of an optically transparent or translucent material in order to perform positioning and confirmation of a compressed state in compression of the breast. In addition, the compression part 42 is preferably formed of a material having excellent transmittance of the radiation R and ultrasonic waves. In addition, the compression part 42 is preferably formed of, for example, a material excellent in strength such as drop strength and compression strength.

As such a material, for example, a resin such as polymethylpentene (PMP), polycarbonate (PC), acryl, polypropylene (PP), and polyethylene terephthalate (PET) can be used. In particular, in the polymethylpentene, acoustic impedance, which affects transmissivity and reflectivity of ultrasonic waves, is close to that of a human body (breast) as compared with other materials, and a proportion of noise on the ultrasound image can be reduced. Therefore, the polymethylpentene is suitable as the material of the compression part 42.

In addition, a plurality of different types of compression members 40 may be attached to the medical image acquisition apparatus 10 in an interchangeable manner. Specifically, according to a physique of the subject (for example, a size of the breast), a tissue composition of the breast (for example, a fat mass and a mammary gland mass), a type of imaging (for example, magnified imaging and spot imaging), and the like, the compression members 40 having different materials, sizes, and shapes may be attached. For example, a compression member according to the size of the breast, a compression member for axillary imaging, a compression member for magnified imaging, a compression member for so-called spot imaging that captures a radiation image of only a region where a lesion exists, and the like may be used. That is, the compression member 40 is not limited to the compression member that compresses the entire breast, and may have a smaller size than the breast to compress a part of the breast.

In addition, an upper surface 43A and/or a breast contact surface 43B of the bottom portion 43 of the compression member 40 may be coated with a gel-like or liquid medium having ultrasound transmittance. As such a medium, for example, a known jelly for an ultrasound examination, which has the acoustic impedance close to the acoustic impedance of the human body (breast), can be applied. That is, the medical image acquisition apparatus 10 may acquire, via the compression member 40, an ultrasound image of the breast being compressed by the compression member 40 in a state of being coated with the gel-like or liquid medium having ultrasound transmittance. In this case, it is possible to suppress entrance of air into an interface between an ultrasound radiation surface of the ultrasound probe 30 and the upper surface 43A and/or an interface between the contact surface 43B and the breast, and it is possible to reduce a difference in acoustic impedance at each interface, so that the proportion of the noise applied to the ultrasound image can be reduced.

On the other hand, in the medical image acquisition guidance system 1 according to the present embodiment, the ultrasound probe 30 is prepared separately from the medical image acquisition apparatus 10. In the medical image acquisition guidance system 1 according to the present embodiment, although the ultrasound probe 30 is connected to the medical image acquisition apparatus 10 in a wired manner (not shown), the present disclosure is not limited to this. The ultrasound probe 30 may have a wireless communication function and may be connected to the medical image acquisition apparatus 10 via the wireless communication function.

The ultrasound probe 30 is used to obtain an ultrasound image of the breast put into the compressed state by the compression member 40, manually performs scanning on the upper surface 43A of the bottom portion 43 of the compression member 40, irradiates the breast with an ultrasonic wave via the compression member 40, and receives a reflected wave from the breast. In addition, the ultrasound probe 30 includes a converter (not shown) that converts the received reflected wave from the breast into the ultrasound image, and the ultrasound image is obtained by the converter.

Specifically, the ultrasound probe 30 comprises an ultrasound transducer array. The ultrasound transducer array has a configuration in which a plurality of ultrasound transducers are arranged one-dimensionally or two-dimensionally. The ultrasound transducer may be constituted, for example, by forming electrodes at both ends of a piezoelectric body such as a piezoelectric ceramic represented by lead zirconate titanate (PZT), a piezoelectric single crystal represented by lead magnesium niobate-lead titanate (PMN-PT), and a polymer piezoelectric element represented by polyvinylidene difluoride (PVDF). In addition, for example, the ultrasound transducer may be a capacitive micro-machined ultrasound transducer (CMUT).

In addition, in the medical image acquisition guidance system 1 according to the present embodiment, a plurality of types of the ultrasound probes 30 different from each other are attached in an interchangeable manner. Specifically, according to a physique of the subject (for example, a size of the breast), a tissue composition of the breast (for example, a fat mass and a mammary gland mass), a type of imaging (for example, magnified imaging and spot imaging), and the like, the ultrasound probes 30 having different performances and dimensions may be attached. For example, a linear probe having a center frequency of about 7.5 MHZ (for superficial use or the like), a convex probe having a center frequency of about 3.5 MHZ (for abdomen or the like), a sector probe having a center frequency of about 2.5 MHZ (for heart or the like), and the like may be used.

Meanwhile, a projector 80 provided with a projection unit 80A is built in an upper portion of the arm part 12 in the vicinity of an exit of the radiation emitted by the radiation emitting unit 17. The projector 80 is mainly configured to project an image (hereinafter, referred to as a "projection image") indicating various types of information onto an upper surface of the compression member 40. On the other hand, in a case in which the compression member 40 is detached, the projector 80 can project a projection image onto an upper surface of the imaging table 16 or the breast in a state of not being compressed by the compression member 40. As the projector 80, known projectors such as a liquid crystal projector, a Digital Light Processing (DLP) (registered trademark) projector, and a laser projector can be used.

A method of imaging the breast using the medical image acquisition apparatus 10 is not particularly limited. For example, cranio-caudal (CC) imaging, medio-lateral oblique (MLO) imaging, magnified imaging and spot imaging for imaging a part of the breast, and the like may be used. The CC imaging is a method of imaging the breast in a compressed state by sandwiching the breast between the imaging table 16 and the compression member 40 in the up-down direction (Z direction). The MLO imaging is a method of imaging the breast in a compressed state, including an axillary portion, by sandwiching the breast between the imaging table 16 and the compression member 40 in a tilted state in which a rotation angle of the arm part 12 with respect to the base 14 is 45 degrees or more and less than 90 degrees.

In addition, for example, the medical image acquisition apparatus 10 may perform tomosynthesis imaging. In the tomosynthesis imaging, the radiation source 17R irradiates the breast with the radiation R from each of a plurality of irradiation positions having different irradiation angles, and a plurality of radiation images of the breast are captured. That is, in the tomosynthesis imaging, the imaging is performed by changing a rotation angle of the radiation emitting unit 17 with respect to the base 14 while angles of the imaging table 16, the compression member 40, the breast, and the like are fixed.

In addition, in the medical image acquisition apparatus 10, the breast of the subject may be positioned not only in a state where the subject is standing up (standing state), but also in a state where the subject is sitting on a chair, a wheelchair, or the like (sitting state).

The console 50 sets an upper limit value of a compression force applied to the breast by the compression member 40 according to the type of the compression member 40 attached to the medical image acquisition apparatus 10. In addition, the console 50 controls the medical image acquisition apparatus 10 to acquire the radiation image and the ultrasound image in accordance with the imaging order acquired from the RIS 6 and the instruction from the user.

The medical image acquisition apparatus 10 according to the present embodiment can acquire both the radiation image and the ultrasound image in a state where the breast is compressed by the compression member 40. As a result, registration between these images is facilitated, and a differential determination ability of the lesion can be improved by displaying both images in a superimposed manner.

Next, the console 50 according to the present embodiment will be described.

Figure 4:
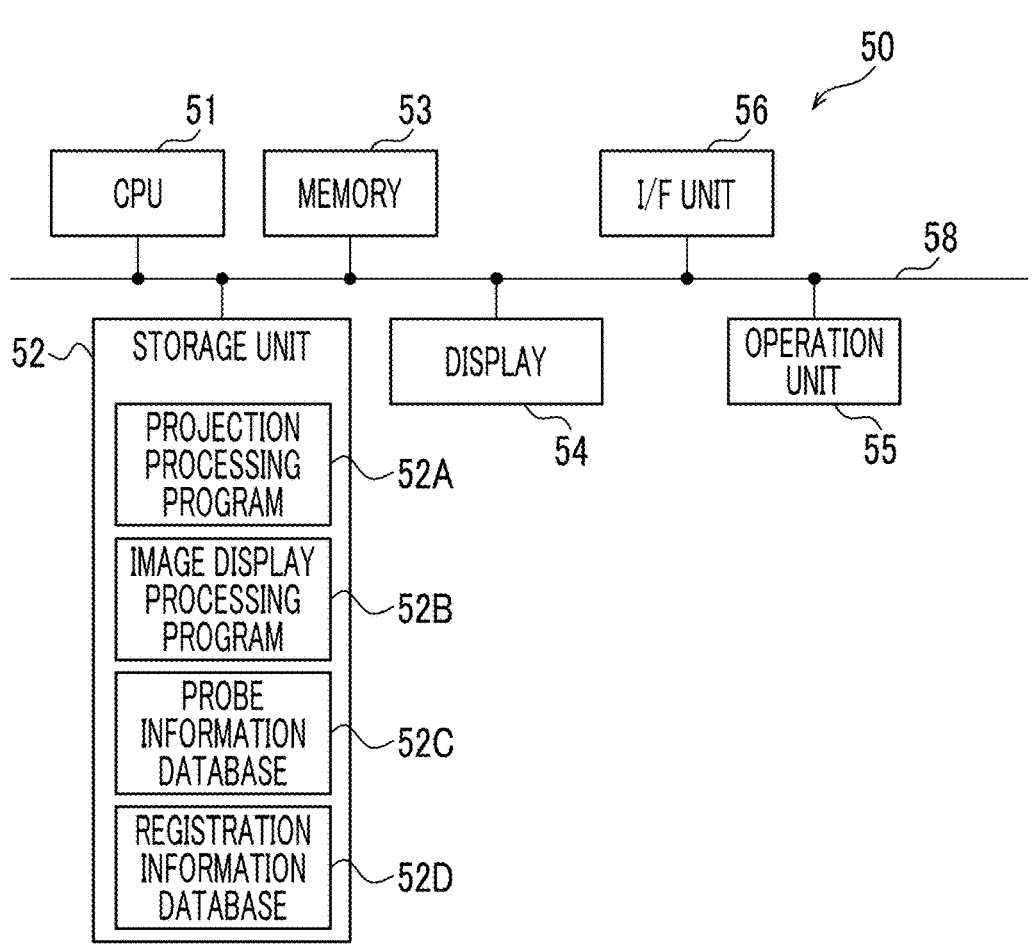
FIG. 4 is a block diagram showing an example of a hardware configuration of a console according to the embodiment.

First, an example of a hardware configuration of the console 50 will be described with reference to FIG. 4. As shown in FIG. 4, the console 50 includes a CPU 51 as a processor, a non-volatile storage unit 52, and a memory 53 as a transitory storage region. In addition, the console 50 includes a display 54 as a display unit such as a liquid crystal display, an operation unit 55 such as a touch panel, a keyboard, and a mouse, and an I/F unit 56. The I/F unit 56 performs wired or wireless communication with the medical image acquisition apparatus 10, the RIS 6, other external devices, and the like. The CPU 51, the storage unit 52, the memory 53, the display 54, the operation unit 55, and the I/F unit 56 are connected to each other via a bus 58 such as a system bus and a control bus, so that various types of information can be exchanged.

The storage unit 52 is implemented by, for example, a storage medium such as an HDD, an SSD, and a flash memory. A projection processing program 52A and an image display processing program 52B are stored in the storage unit 52. The CPU 51 appropriately reads out each of the projection processing program 52A and the image display processing program 52B from the storage unit 52, loads the read-out program into the memory 53, and executes each loaded program. As the console 50, for example, a personal computer, a server computer, a smartphone, a tablet terminal, or a wearable terminal can be appropriately applied.

In addition, a probe information database 52C and a registration information database 52D are stored in the storage unit 52. Details of the probe information database 52C and the registration information database 52D will be described below.

Figure 5:
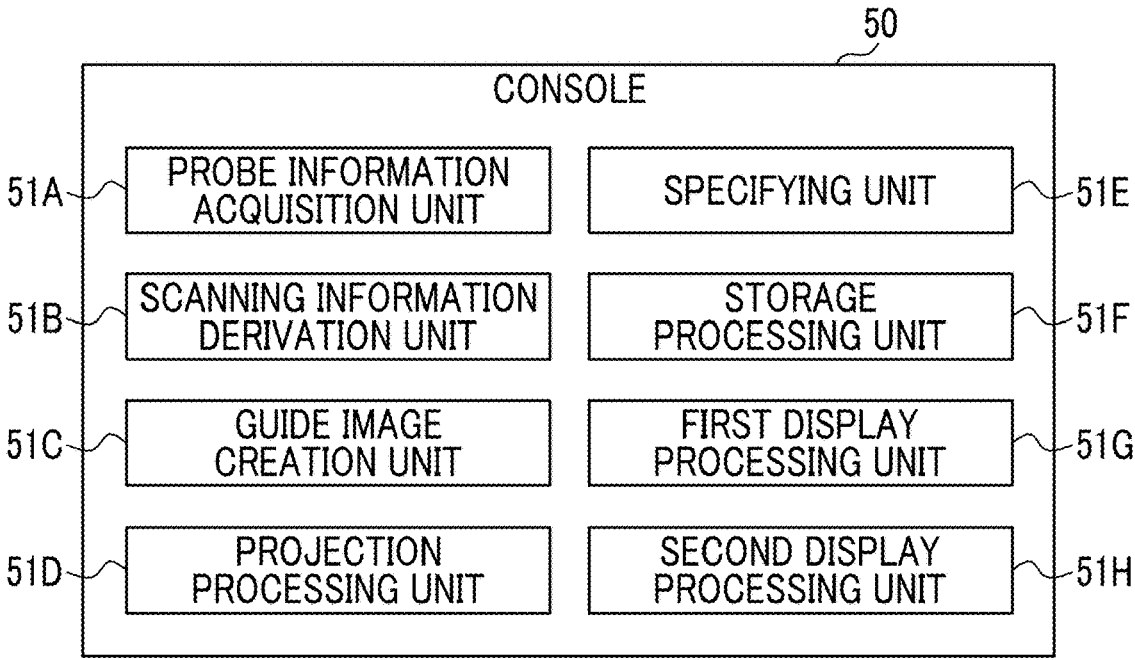
FIG. 5 is a block diagram showing an example of a functional configuration of the console according to the embodiment.

Next, an example of a functional configuration of the console 50 will be described with reference to FIG. 5. As shown in FIG. 5, the console 50 includes a probe information acquisition unit 51A, a scanning information derivation unit 51B, a guide image creation unit 51C, a projection processing unit 51D, a specifying unit 51E, a storage processing unit 51F, a first display processing unit 51G, and a second display processing unit 51H. The CPU 51 executes the projection processing program 52A, so that the CPU 51 functions as the probe information acquisition unit 51A, the scanning information derivation unit 51B, the guide image creation unit 51C, the projection processing unit 51D, the specifying unit 51E, and the storage processing unit 51F. In addition, the CPU 51 executes the image display processing program 52B, so that the CPU 51 functions as the first display processing unit 51G and the second display processing unit 51H.

In a case in which a radiation image and an ultrasound image of the breast in a state of being compressed by the compression member 40 are captured, the probe information acquisition unit 51A according to the present embodiment acquires information (hereinafter, referred to as "probe information") including an effective width of the ultrasound probe 30 in capturing the ultrasound image. Here, the term "effective width" means a width of a region of the ultrasound probe 30 where an ultrasonic wave can be transmitted and received.

In addition, the scanning information derivation unit 51B according to the present embodiment derives information (hereinafter, referred to as "scanning information") indicating at least one of a scanning region or a scanning direction of the ultrasound probe 30 according to the effective width in the acquired probe information. The scanning information derivation unit 51B according to the present embodiment derives both the scanning region and the scanning direction, but the present disclosure is not limited to this. For example, the scanning information derivation unit 51B may be configured to derive only one of the scanning region or the scanning direction.

In addition, the guide image creation unit 51C according to the present embodiment uses at least one of the scanning region or the scanning direction indicated by the derived scanning information to create a guide image for guiding at least one of the scanning region or the scanning direction.

Then, the projection processing unit 51D according to the present embodiment performs processing of projecting the created guide image onto the side of the compression member 40 opposite to the compression side of the breast, that is, onto the upper surface 43A of the bottom portion 43 of the compression member 40.

In addition, the specifying unit 51E according to the present embodiment specifies at least one of an actual scanning region or an actual scanning direction using a detection result of a position sensor (not shown) that detects a position of the ultrasound probe 30. Then, the storage processing unit 51F according to the present embodiment performs processing of storing the ultrasound image obtained by scanning using the ultrasound probe 30 and at least one of the scanning region or the scanning direction specified by the specifying unit 51E in the scanning for obtaining the ultrasound image in association with each other.

In the present embodiment, a magnetic sensor formed by combining a magnetic generator and a magnetic position sensor is applied as the position sensor, but the present disclosure is not limited to this. For example, an optical position sensor, an electric position sensor, or the like may be applied as the position sensor.

As described above, in the present embodiment, at least one of the scanning region or the scanning direction stored by the storage processing unit 51F is detected by the position sensor, but the present disclosure is not limited to this. For example, a form may be adopted in which an optical camera that images the upper surface side of the compression member 40 is prepared, and at least one of the scanning region or the scanning direction is detected by an image analysis technique for an image captured by the optical camera.

In addition, an ultrasound image obtained in a state where the ultrasound probe 30 is in contact with the compression member 40 is a normal image, but an ultrasound image obtained in a state where the ultrasound probe 30 is separated from the compression member 40 is an image in a state where multiple echoes from the upper surface 43A of the bottom portion 43 of the compression member 40 are repeated. Therefore, for example, a form may be adopted in which a change in the state of the ultrasound image obtained by the scanning using the ultrasound probe 30 is utilized to detect whether the ultrasound probe 30 is separated from the compression member 40, and the detection result is used to detect at least one of the scanning region or the scanning direction.

On the other hand, in a case in which the ultrasound image is stored in association with the scanning region, the first display processing unit 51G according to the present embodiment performs first display processing of displaying the radiation image corresponding to the ultrasound image together with a scanning region image which is an image showing the scanning region. Then, in a case in which the scanning region shown in the scanning region image displayed by the first display processing is designated by the user, the second display processing unit 51H according to the present embodiment performs second display processing of displaying the ultrasound image corresponding to the scanning region.

Here, in a case in which scanning using the ultrasound probe 30 is performed a plurality of times to capture a single ultrasound image, the scanning information derivation unit 51B according to the present embodiment decides the scanning regions corresponding to scans adjacent to each other such that the adjacent regions overlap each other within a predetermined range. In this case, it is preferable that the overlapping range is generally in a range of 5 mm to 10 mm. This is because an overlap of about 5 mm is necessary in order to reliably cause the ultrasound probe 30 to perform scanning in a manual procedure, and an overlap of about 10 mm is necessary in consideration of higher safety, while the number of times of scanning is excessively increased in a case in which the overlap exceeds 10 mm. A probe width of the ultrasound probe 30 (corresponding to the effective width described above) is generally about 35 mm to 50 mm, and a range of 5 mm to 10 mm corresponds to about 10% to 30% of the probe width.

In the present embodiment, an image including a line, a mark, and a character is applied as the guide image, but the present disclosure is not limited to this. For example, an image further including a figure may be applied as the guide image, and an image including one of the line, the figure, the mark, or the character or an image including a plurality of combinations excluding all of the line, the figure, the mark, and the character may be applied as the guide image.

In the present embodiment, the probe information acquisition unit 51A acquires the above-described effective width at a timing at which the ultrasound probe 30 is attached to the medical image acquisition apparatus 10, but the present disclosure is not limited to this. For example, the effective width may be acquired at any one of a timing at which the medical image acquisition apparatus 10 or the console 50 is powered on or a timing at which a preset for acquiring an image showing the breast is selected.

Next, the probe information database 52C according to the present embodiment will be described with reference to FIG. 6. FIG. 6 is a schematic diagram showing an example of a configuration of the probe information database 52C according to the present embodiment.

The probe information database 52C according to the present embodiment is a database in which the above-described probe information, which is information related to a size of a predetermined type of ultrasound probe applicable to the medical image acquisition apparatus 10, is registered. As shown in FIG. 6 as an example, in the probe information database 52C according to the present embodiment, a probe identification (ID) and each piece of probe information are stored in association with each other.

The probe ID is information assigned in advance to be different for each ultrasound probe applicable to the medical image acquisition apparatus 10 in order to identify each ultrasound probe. In addition, the probe information is information indicating a size of a corresponding ultrasound probe, and includes two sizes of a probe width and a housing width. Here, the probe width is information indicating the above-described effective width of the corresponding ultrasound probe, and the housing width is information indicating the width of the housing itself of the corresponding ultrasound probe.

In the example shown in FIG. 6, it is shown that the probe width (effective width) of the ultrasound probe to which "P001" is assigned as the probe ID is 50 mm, and the housing width is 52 mm. Accordingly, the ultrasound probe has a housing region of 1 mm on each of both end sides of a region in which an ultrasonic wave can be transmitted and received in the ultrasound probe.

Next, the registration information database 52D according to the present embodiment will be described with reference to FIG. 7. FIG. 7 is a schematic diagram showing an example of a configuration of the registration information database 52D according to the present embodiment.

The registration information database 52D according to the present embodiment is a database in which the radiation image and the ultrasound image acquired by the medical image acquisition apparatus 10 are registered. As shown in FIG. 7 as an example, in the registration information database 52D according to the present embodiment, the radiation image and each piece of registration information are stored in association with each other.

The radiation image is information indicating the radiation image itself acquired by imaging with the medical image acquisition apparatus 10. In addition, the registration information is information related to an ultrasound image acquired by imaging with the ultrasound probe 30 in the same state as a state where a corresponding radiation image is captured, and includes information on a probe ID, an ultrasound image, a scanning region, and a scanning direction of the ultrasound probe 30.

That is, the ultrasound probe applicable to the medical image acquisition apparatus 10 according to the present embodiment is set such that the effective width thereof is shorter than a width in a depth direction (left-right direction in FIG. 2) on the upper surface 43A of the bottom portion 43 of the compression member 40. Therefore, a plurality of times of scanning are required in order to acquire ultrasound images corresponding to the entire region of the upper surface 43A.

The ultrasound image, the scanning region, and the scanning direction in the registration information are information registered for each of the plurality of times of scanning. In the example shown in FIG. 7, a case is illustrated in which ultrasound images corresponding to capturing of a radiation image A were captured four times using the ultrasound probe 30 to which "P001" is assigned as the probe ID.

In the present embodiment, an ultrasound image of a video image is applied as the ultrasound image registered in the registration information database 52D, but the present disclosure is not limited to this. For example, an ultrasound image of a still image is registered as the ultrasound image in the registration information database 52D.

Next, an operation of the medical image acquisition guidance system 1 according to the present embodiment will be described with reference to FIGS. 8 to 18. First, an operation of the console 50 in a case in which the projection processing is executed will be described with reference to FIGS. 8 to 15. In the console 50, the CPU 51 executes the projection processing program 52A to execute the projection processing shown in FIG. 8. The projection processing according to the present embodiment is executed in a case in which a user, such as a doctor or technician, connects the ultrasound probe 30 to be used to the medical image acquisition apparatus 10 and issues an instruction to start execution via the operation unit 55 in order to, after the radiation image is captured in a state where the breast is compressed by the compression member 40 in the medical image acquisition apparatus 10, capture an ultrasound image corresponding to the radiation image. Here, in order to avoid confusion, a case will be described in which the probe information database 52C has already been constructed and the radiation image obtained by the capturing has already been registered in the registration information database 52D.

In step S100, the CPU 51 receives information (in the present embodiment, the probe ID) for specifying the ultrasound probe 30 currently connected from the medical image acquisition apparatus 10. Then, the CPU 51 acquires the probe information corresponding to the received probe ID by reading out the probe information from the probe information database 52C.

Figure 9:
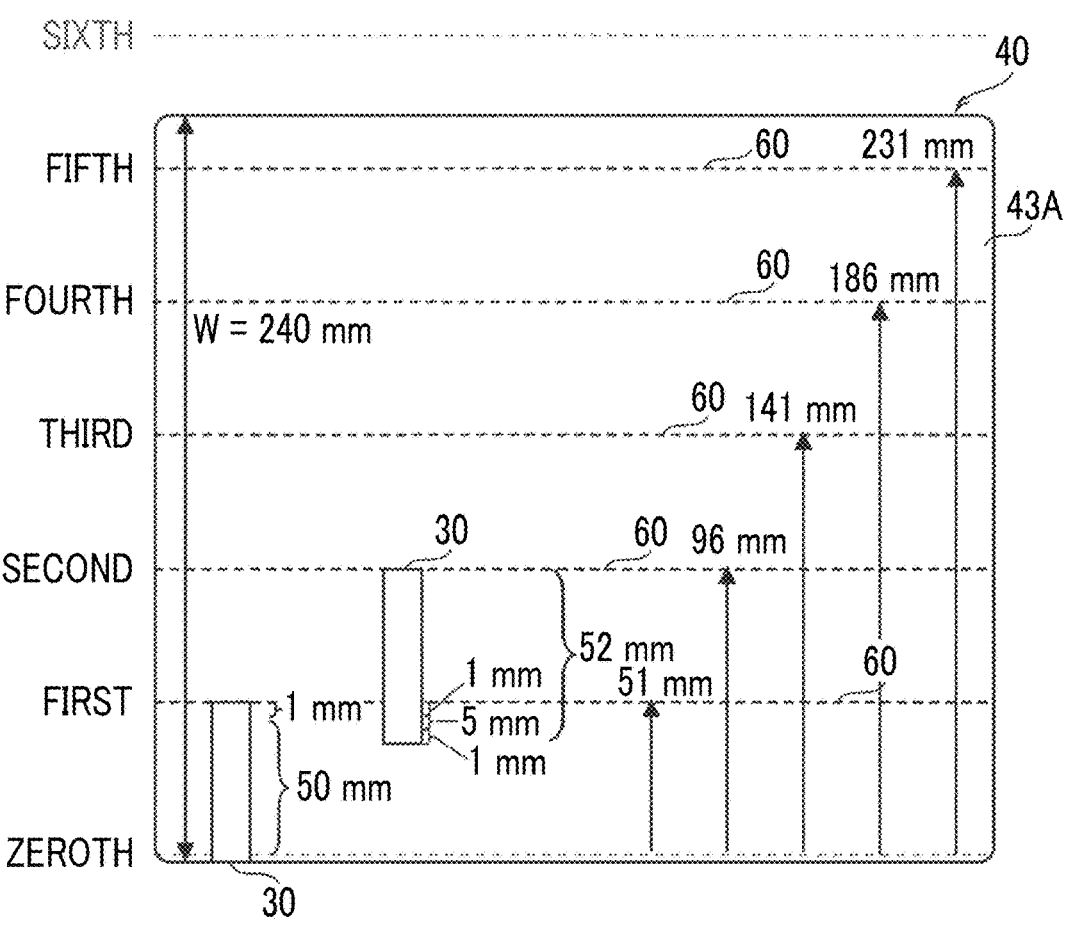
FIG. 9 is a schematic diagram for describing a method of deriving a scanning region according to the embodiment.

In step S102, the CPU 51 derives the above-described scanning information (in the present embodiment, information indicating the scanning region and the scanning direction). First, a specific method of deriving the scanning region according to the present embodiment will be described with reference to FIG. 9. FIG. 9 is a schematic diagram for describing a method of deriving the scanning region according to the present embodiment.

As shown in FIG. 9, first, the CPU 51 virtually sets a region dividing line 60, which is a line indicating an end part of the scanning region of the ultrasound probe 30 and is a line closest to a chest wall side of the subject, to a 0th (zeroth) region dividing line 60 and sets a position of the 0th region dividing line 60 to 0 mm.

Next, the CPU 51 calculates the position of the region dividing line 60 corresponding to the first scanning region of the ultrasound probe 30 according to Equation (1). In Equation (1), PW represents a probe width (effective width) the ultrasound probe 30, HW represents a housing width of the ultrasound probe 30, and L1 represents a position of the region dividing line 60 corresponding to the first scanning region.

$$L1 = PW + (HW - PW)/2 \qquad (1)$$

Then, the CPU 51 calculates the position of the region dividing line 60 corresponding to the second or subsequent scanning region of the ultrasound probe 30 according to Equation (2) on a condition in which a width W in the depth direction on the upper surface 43A of the bottom portion 43 of the compression member 40 is not exceeded. In Equation (2), BL represents a position of the region dividing line 60 corresponding to the previous scanning region, DW represents an overlap width with an adjacent scanning region in a case of performing scanning using the ultrasound probe 30, and Ln represents a position of the region dividing line 60 corresponding to the scanning region in which the nth scanning is performed.

$$Ln = BL + (PW - DW) \qquad (2)$$

For example, in a case in which the width W in the depth direction of the upper surface 43A of the bottom portion 43 of the compression member 40 is 240 mm, the probe width PW of the ultrasound probe 30 is 50 mm, the housing width HW of the ultrasound probe 30 is 52 mm, and the overlap width DW with an adjacent scanning region in a case of performing scanning using the ultrasound probe 30 is 5 mm, the position of each region dividing line 60 is as shown in Table 1 below.

TABLE 1

| Region dividing line | Position (mm) |
| --- | --- |
| Zeroth line | 0 |
| First line | 51 |
| Second line | 96 |
| Third line | 141 |
| Fourth line | 186 |
| Fifth line | 231 |

In addition, in the present embodiment, as the scanning direction, a first pattern in which the scanning direction is switched for each scan, a second pattern in which the direction from a left end side to a right end side of FIG. 9 is used in all the scans, and a third pattern in which a direction from the right end side to the left end side of FIG. 9 is used in all the scans are prepared. In the present embodiment, the user designates in advance which of the above three patterns is to be applied. However, the present disclosure is not limited to this aspect, and a form may be adopted in which the CPU 51 decides and applies a suitable scanning direction depending on the purpose of the ultra-sonography, the medical condition of the subject, or the like.

Figure 10:
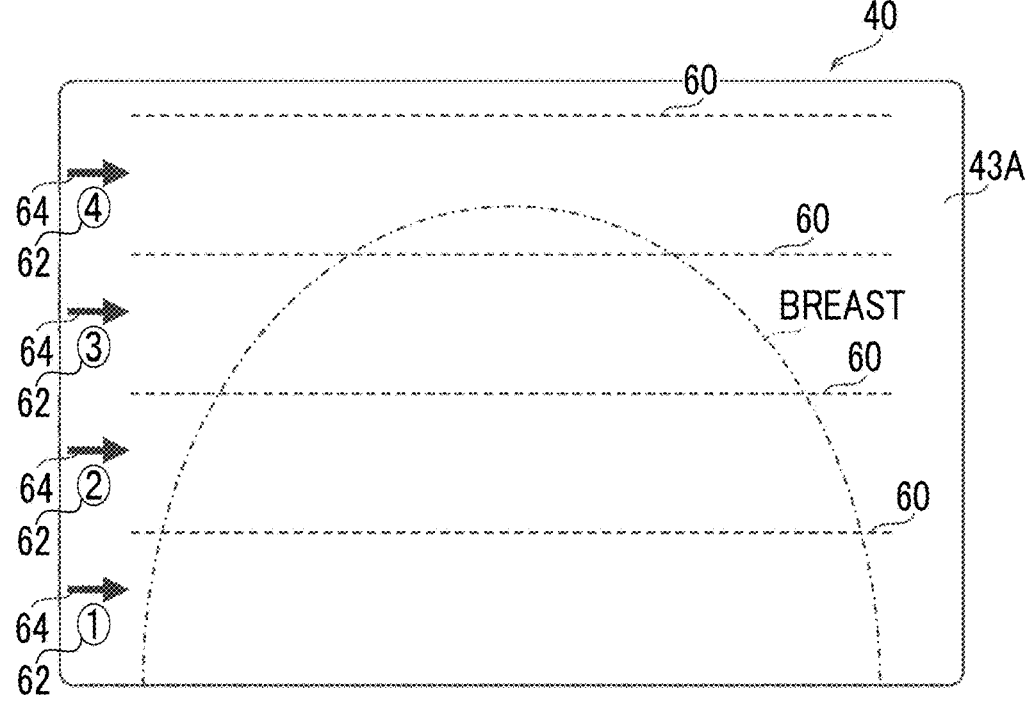
FIG. 10 is a diagram showing an example of a guide image according to the embodiment.

In step S104, the CPU 51 uses the scanning information obtained by the above processing to create information indicating a guide image having a predetermined configuration. In step S106, the CPU 51 controls the projector 80 such that the guide image indicated by the created information is projected onto the upper surface 43A of the bottom portion 43 of the compression member 40. Through this control, the guide image is projected onto the upper surface 43A of the bottom portion 43 of the compression member 40. FIG. 10 shows an example of the guide image according to the present embodiment. FIG. 10 illustrates a case in which the number of the region dividing lines 60, that is, the number of times of scanning is four.

Figure 11:
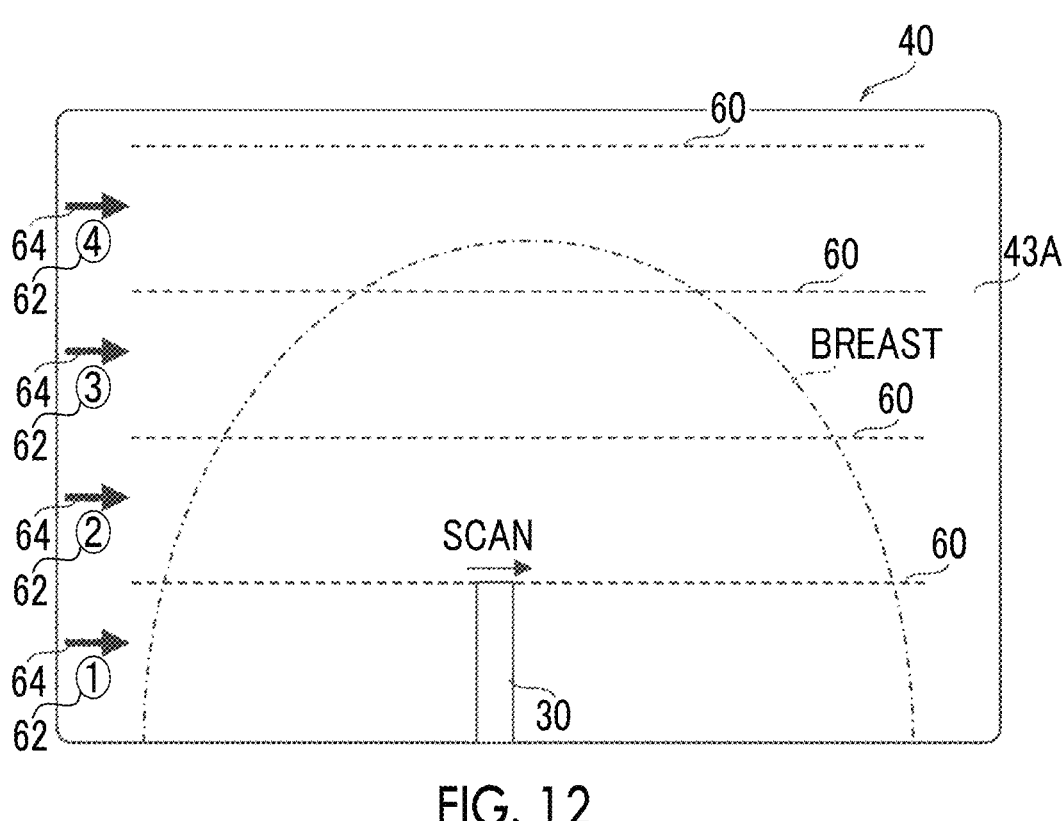
FIG. 11 is a diagram showing an example of a scanning state of an ultrasound probe according to the guide image according to the embodiment.

As shown in FIG. 10, in the guide image according to the present embodiment, the projection is performed in a state where the scanning region for each of the plurality of times of scanning of the ultrasound probe 30 is divided by the region dividing line 60 (in the example shown in FIG. 10, four divisions). In addition, in the guide image, a number 62 indicating the operation order and an arrow 64 indicating the scanning direction are projected for each of the respective divisions. Accordingly, the user can grasp the scanning region and the scanning direction of the ultrasound probe 30 by referring to the guide image, and as a result, scanning is performed using the ultrasound probe 30 as shown in FIG. 11 as an example. FIG. 11 illustrates a case in which the ultrasound probe 30 is in the middle of the first scanning.

Figure 12:
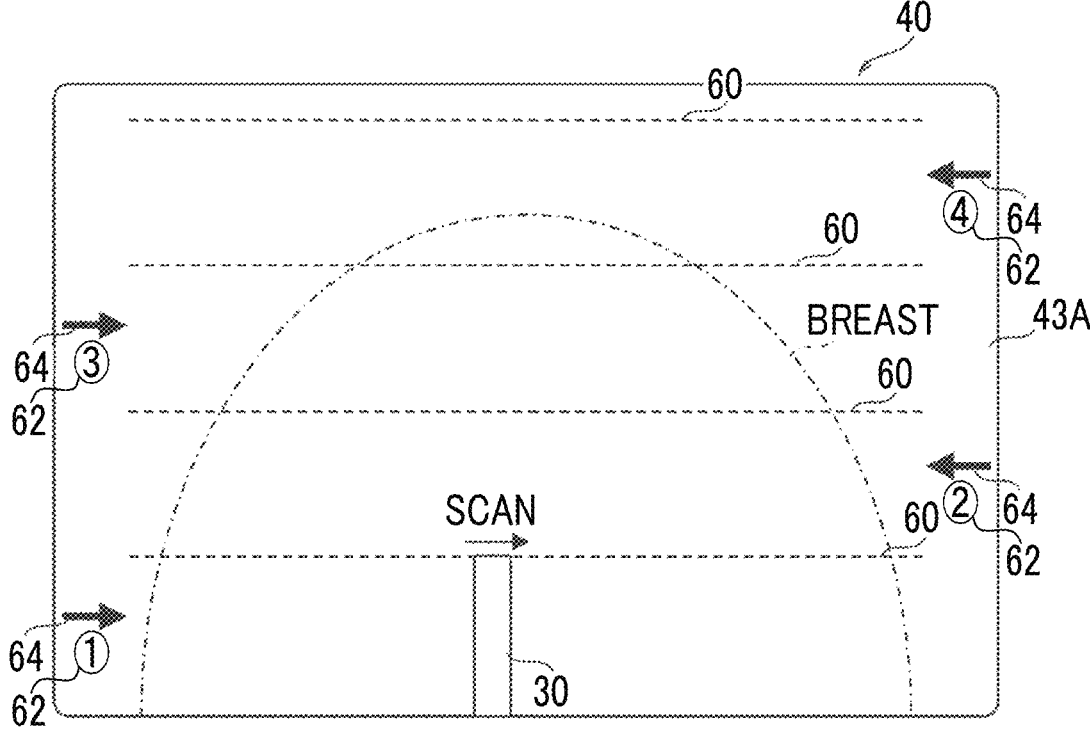
FIG. 12 is a diagram showing another example of the guide image according to the embodiment.

Although FIGS. 10 and 11 illustrate the guide image in a case in which the second pattern is selected as the scanning direction, the present disclosure is not limited to this. For example, in a case in which the first pattern is selected as the scanning direction, a guide image shown in FIG. 12 is projected as an example. In the guide image, a case is illustrated in which the odd-numbered scanning direction is a direction from the left end side to the right end side, and the even-numbered scanning direction is a direction from the right end side to the left end side.

Figure 13:
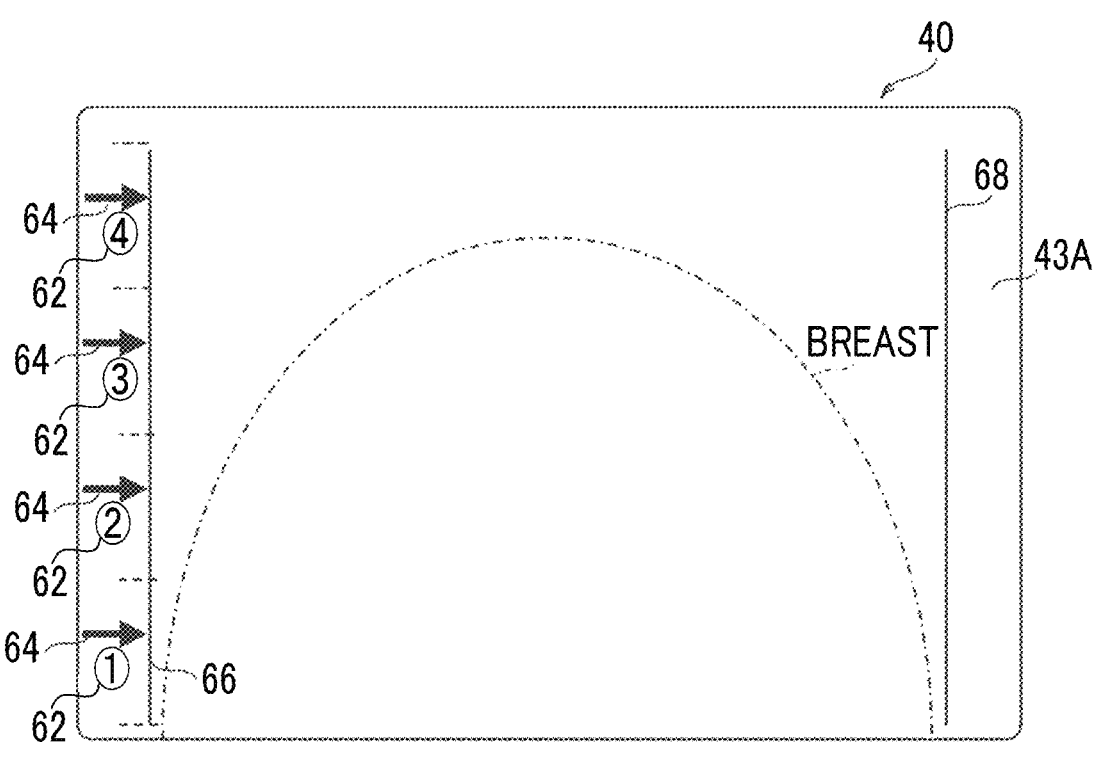
FIG. 13 is a diagram showing still another example of the guide image according to the embodiment.
Figure 14:
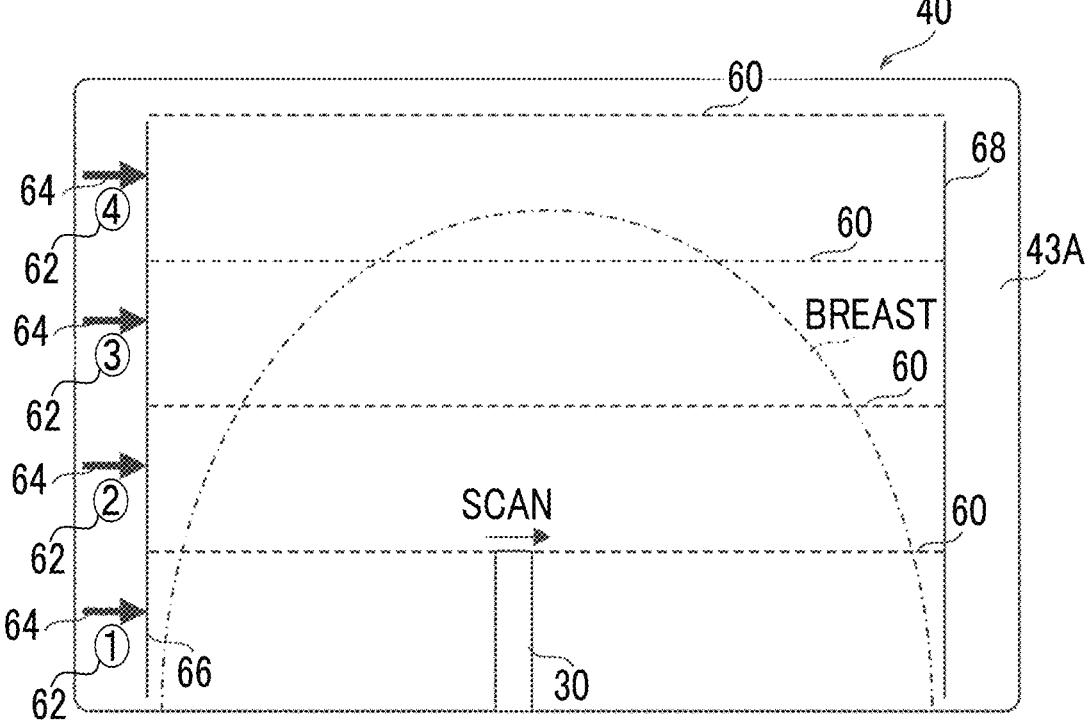
FIG. 14 is a diagram showing still another example of the guide image according to the embodiment.

In addition, as shown in FIG. 13 as an example, a form may be adopted in which a scanning start line 66 indicating a scanning start position of the ultrasound probe 30 and a scanning end line 68 indicating a scanning end position of the ultrasound probe 30 are projected as the guide image. In addition, as shown in FIG. 13, a form may be adopted in which the region dividing line 60 between the scanning start line 66 and the scanning end line 68 is not projected. According to this aspect, it is possible to prevent the region dividing line 60 from interfering the visual recognition of the user. Further, as shown in FIG. 14 as an example, it is needless to say that a form may be adopted in which the scanning start line 66 and the scanning end line 68 are added to the guide image shown in FIGS. 11 and 12 and projected.

In step S108, the CPU 51 waits until one scan of the ultrasound probe 30 is ended, based on the position of the ultrasound probe 30 obtained by the above-described position sensor.

In step S110, the CPU 51 derives information indicating the actual scanning region and the actual scanning direction of the ultrasound probe 30 from the position of the ultrasound probe 30 obtained by the position sensor. Then, the CPU 51 stores (registers) the derived information and the ultrasound image obtained by scanning using the ultrasound probe 30 in a corresponding storage region of the registration information database 52D together with the probe ID of the ultrasound probe 30. The registration of the probe ID performed here need only be performed only at the end of the first scanning.

In step S112, the CPU 51 determines whether or not all the scans of the ultrasound probe 30 are ended, and, in a case in which the determination result is negative, the process returns to step S108.

Through the above processing in steps S108 to S112, information related to the ultrasound image in substantially the same region as the corresponding radiation image is registered in the registration information database 52D.

On the other hand, in a case in which the determination result in step S112 is positive, that is, in a case in which all the scans of the ultrasound probe 30 are ended, the process proceeds to step S114, and the CPU 51 stops the projection of the guide image and then ends the present projection processing.

In a case in which the above projection processing is being executed, the ultrasound image acquired in response to the scanning using the ultrasound probe 30 is displayed on the display 54 of the console 50 in real time as a video image of approximately 10 images/sec. As a display form in an overlapping region with adjacent ultrasound images in this case, a form in which only one of the images is displayed, a form in which an image obtained by weighting both images is displayed, and the like are illustrated. In addition, in this form, a form may be adopted in which an image similar to the projected guide image is superimposed on the ultrasound image and displayed on the display 54.

On the other hand, the medical image acquisition apparatus 10 or the console 50 may be provided with a freeze key that is pressed in a case in which the display state of the ultrasound image displayed on the display 54 is switched between the video image and the still image. In this case, the operation of switching the display state of the ultrasound image by the freeze key in a case in which scanning is performed using the ultrasound probe 30 is generally as follows.

In a case in which scanning is started, the display state of the ultrasound image is set to a video image by the default or freeze key operation.→The first scanning is executed.→At the end of the scanning, the display state of the ultrasound image is set to a still image by the freeze key operation.→The still image is read.→At the end of the reading, the display state of the ultrasound image is set to a video image by the freeze key operation.→The second scanning is executed. Thereafter, the freeze key operation is repeated until the scanning is ended in the same manner.

Figure 15:
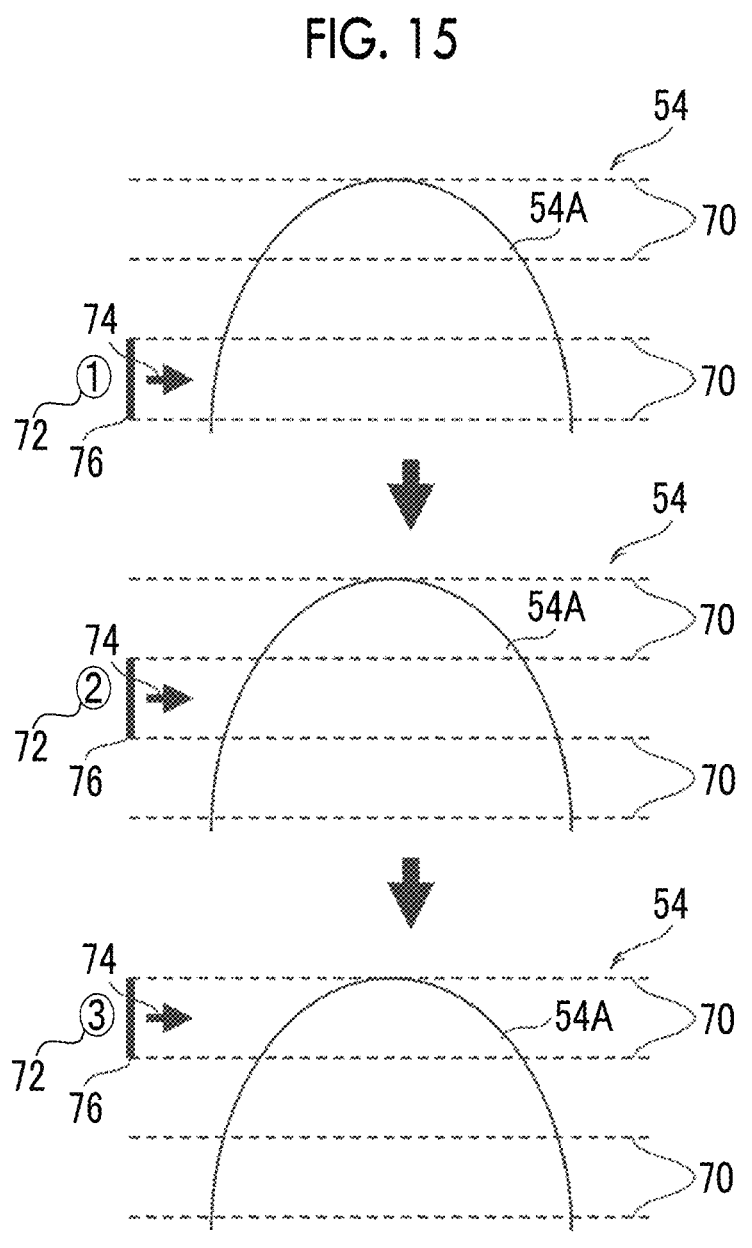

In this case, in parallel with the projection processing, as shown in FIG. 15 as an example, a form may be adopted in which a body mark 54A is displayed on a part of the display 54 of the console 50, and a region dividing line 70, a number 72, an arrow 74, and a scanning start line 76, which have roles similar to those of the region dividing line 60, the number 62, and the arrow 64 described above, are displayed on the body mark 54A. In addition, in this form, as shown in FIG. 15, a form may be adopted in which, for each of the plurality of times of scanning, the number 72, the arrow 74, and the scanning start line 76 related to the corresponding scanning are displayed at a timing of performing the corresponding scanning.

Figure 16:
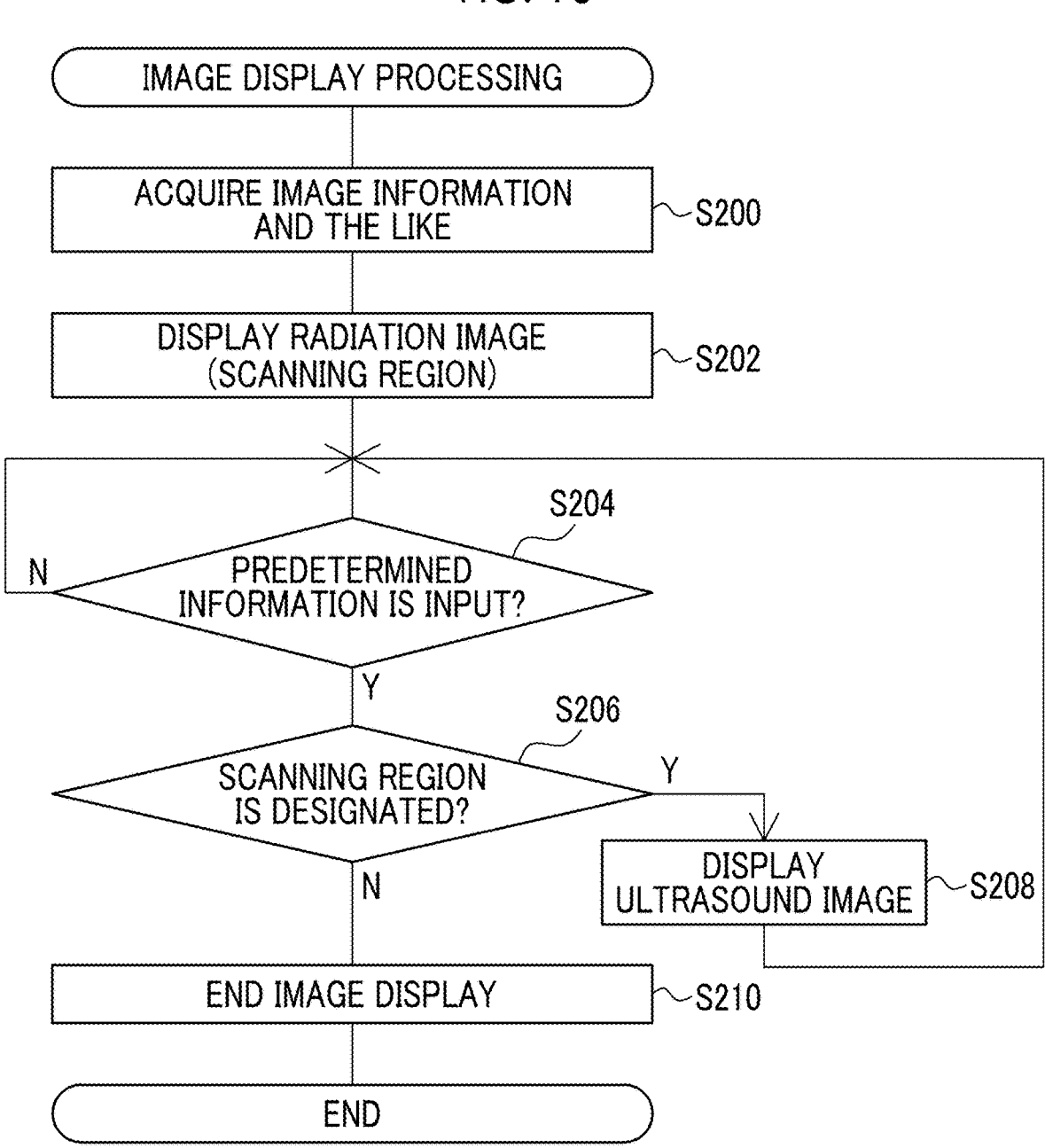
FIG. 16 is a flowchart showing an example of image display processing according to the embodiment.

Next, an operation of the console 50 in a case in which image display processing is executed will be described with reference to FIGS. 16 to 18. In the console 50, the CPU 51 executes the image display processing program 52B to execute the image display processing shown in FIG. 16. The image display processing according to the present embodiment is executed in a case in which a user, such as a doctor or a technician, issues an instruction to start execution via the operation unit 55 in order to display the radiation image and the ultrasound image acquired by the medical image acquisition apparatus 10. Here, in order to avoid confusion, a case will be described in which the registration information database 52D has already been constructed and information indicating the radiation image to be displayed by the main image display processing has already been designated.

In step S200, the CPU 51 reads out the radiation image indicated by the designated information (hereinafter, referred to as a "display target radiation image") and registration information corresponding to the display target radiation image from the registration information database 52D.

In step S202, the CPU 51 uses the read information to control the display 54 to display a radiation image display screen having a predetermined configuration, and, in step S204, the CPU 51 waits until predetermined information is input. FIG. 17 shows an example of a display state of the radiation image display screen according to the present embodiment.

Figure 17:
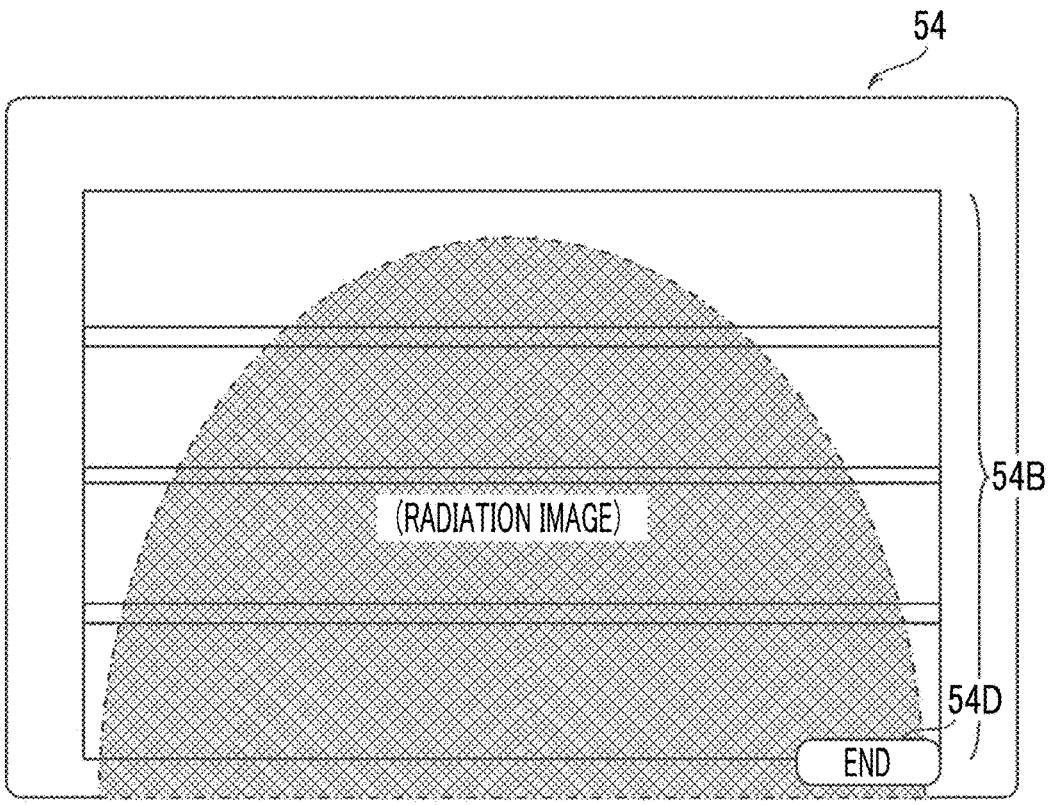
FIG. 17 is a diagram showing an example of a display state of a radiation image display screen according to the embodiment.

As shown in FIG. 17, on the radiation image display screen according to the present embodiment, the display target radiation image is displayed, and a scanning region image 54B indicating a corresponding scanning region is displayed.

Therefore, in a case in which the user wants to display the ultrasound image corresponding to any scanning region in the displayed display target radiation image, the user designates the corresponding scanning region, and, in a case in which the user wants to end the display of the image, the user designates an end button 54D, via the operation unit 55. In a case in which any scanning region or the end button 54D is designated by the user, the determination result in step S204 is positive, and the process proceeds to step S206.

In step S206, the CPU 51 determines whether or not any scanning region is designated by the user, and, in a case in which the determination result is positive, the process proceeds to step S208. In step S208, the CPU 51 controls the display 54 such that a superimposed ultrasound image display screen on which the ultrasound image corresponding to the scanning region designated by the user (hereinafter, referred to as a "designated ultrasound image") is displayed by being superimposed on the designated scanning region of the display target radiation image is displayed instead of the previous screen, and then the process returns to step S204. FIG. 18 shows an example of a display state of the superimposed ultrasound image display screen according to the present embodiment.

Figure 18:
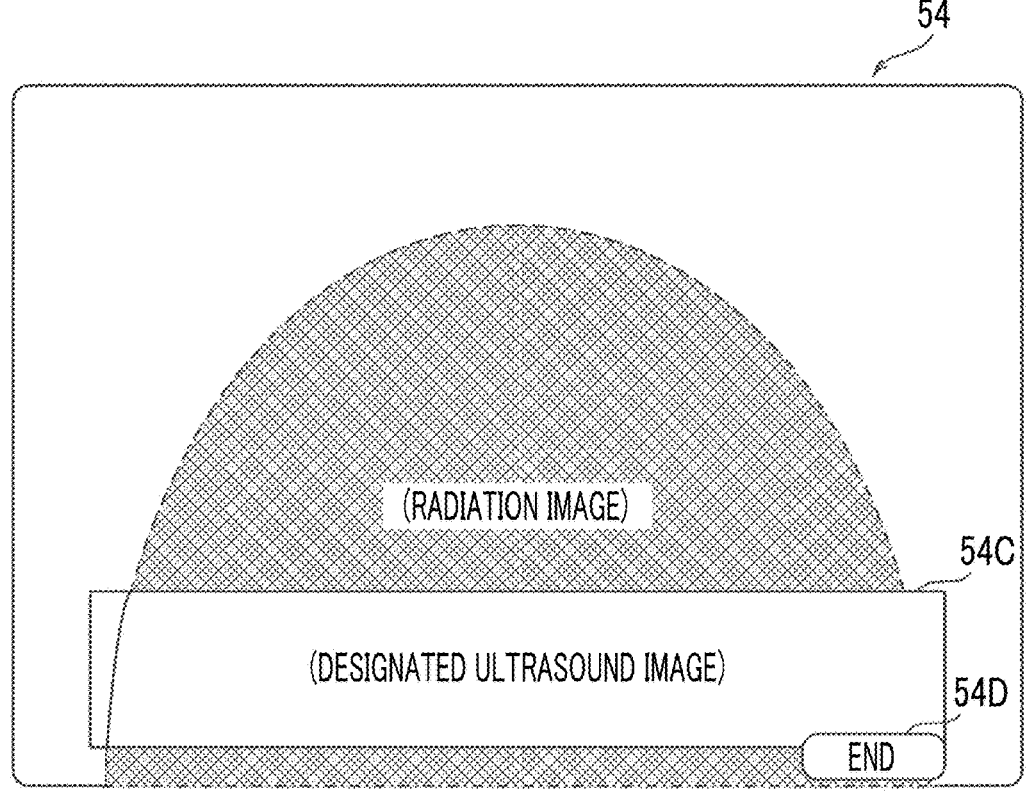
FIG. 18 is a diagram showing an example of a display state of a superimposed ultrasound image display screen according to the embodiment.

As shown in FIG. 18, on the superimposed ultrasound image display screen according to the present embodiment, the designated ultrasound image corresponding to the scanning region designated by the user is displayed in a state of being superimposed on a corresponding region of the radiation image. Therefore, the user can compare the designated ultrasound image with a radiation image of a region adjacent to the designated ultrasound image by referring to the superimposed ultrasound image display screen.

On the other hand, in a case in which the determination result in step S206 is negative, it is assumed that the end button 54D is designated by the user, and the process proceeds to step S210, in which the CPU 51 ends the display of the image currently displayed and then ends the main image display processing.

Figure 19:
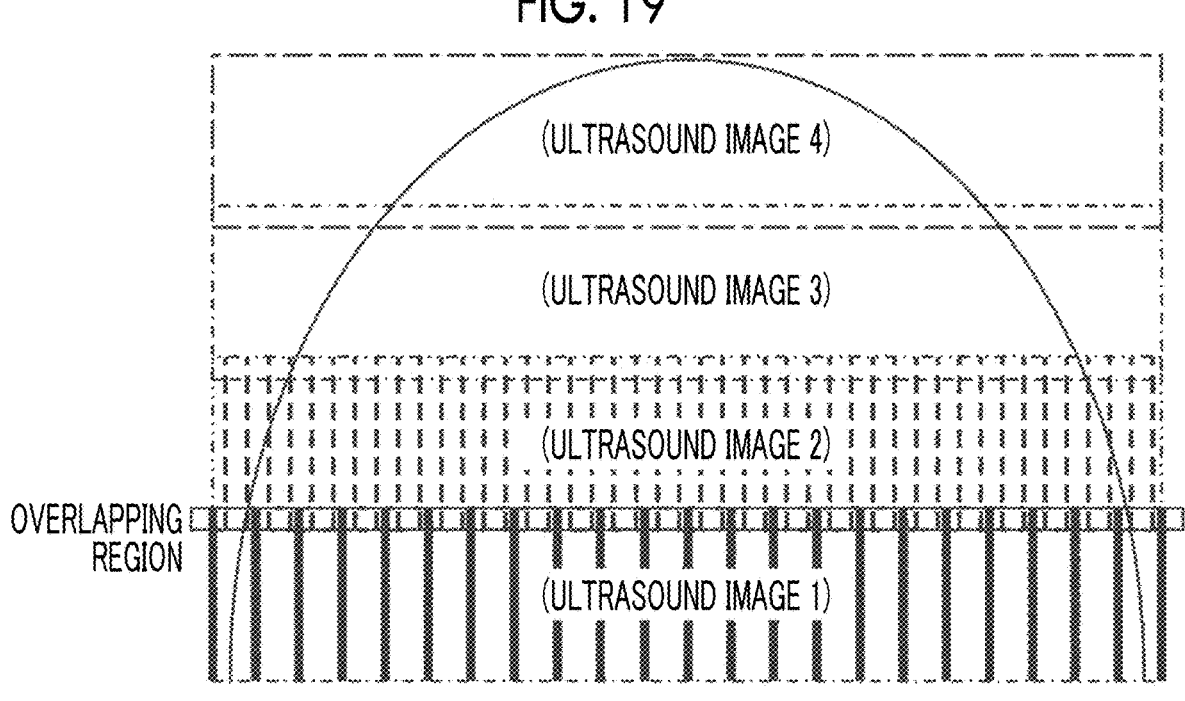
FIG. 19 is a diagram for describing combination of ultrasound images according to the embodiment.

A composite ultrasound image may be generated by combining the ultrasound images for each scanning region registered in the registration information database 52D. Hereinafter, a method of generating the composite ultrasound image will be described with reference to FIGS. 19 and 20A and 20B. FIG. 19 is a diagram for describing the combination of the ultrasound images according to the present embodiment, and FIGS. 20A and 20B are partially enlarged views for describing the combination of the ultrasound images according to the present embodiment.

As shown in FIG. 19 as an example, in a case in which the ultrasound probe 30 performs scanning a plurality of times, a timing at which the ultrasound image is obtained often shifts due to a difference in scanning speed or the like in each scanning. Therefore, in the present embodiment, pattern matching is performed between the ultrasound images in an overlapping region between adjacent scans, and the ultrasound image corresponding to an overlapping region having the highest rate of match is decided as the ultrasound image to be combined.

Figure 20A:
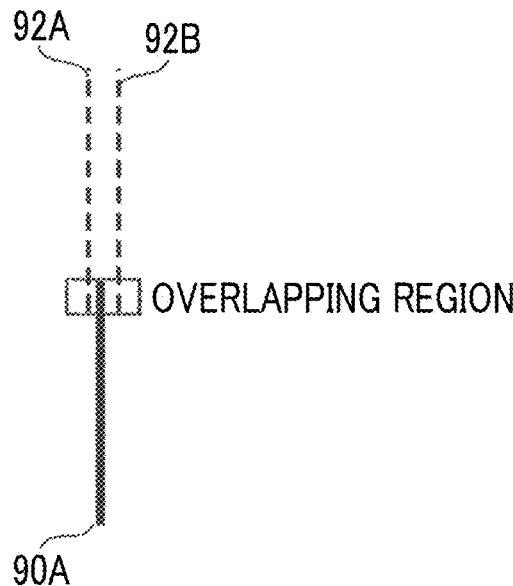
FIG. 20A is a partially enlarged view for describing the combination of ultrasound images according to the embodiment.
Figure 20B:
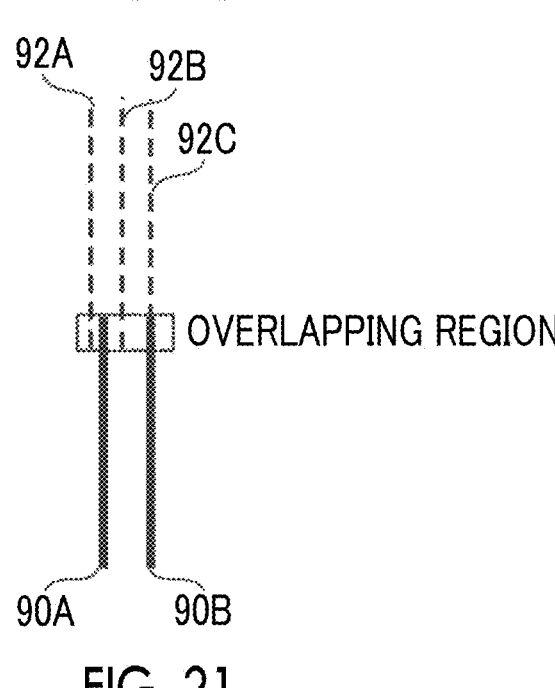
FIG. 20B is a partially enlarged view for describing the combination of ultrasound images according to the embodiment.

For example, as shown in FIG. 20A as an example, in a case in which an ultrasound image 92A is one ultrasound image having the highest rate of match of the overlapping region with the other ultrasound image 90A corresponding to the overlapping region, the ultrasound image 90A and ultrasound image 92A are combined. In addition, as shown in FIG. 20B as an example, in a case in which an ultrasound image 90A is one ultrasound image having the highest rate of match of the overlapping region with the other ultrasound image 92B, the ultrasound image 92B and the ultrasound image 90A are combined even though the ultrasound image 90A is used for combination with another ultrasound image.

The composite ultrasound image obtained by the above combination can be used to generate an image of any cross section of the breast, a three-dimensional image, or the like.

As described above, according to the present embodiment, in a case in which the radiation image and the ultrasound image of the breast in a state of being compressed by the compression member are captured, in capturing the ultrasound image, processing of projecting the guide image for guiding at least one of the scanning region or the scanning direction of the ultrasound probe used for capturing the ultrasound image onto the side of the compression member opposite to the compression side of the breast according to an effective width, which is a region in which transmission and reception of an ultrasonic wave are possible, of the ultrasound probe, is performed. Accordingly, it is possible to perform ultrasonography in a state where the breast is compressed by the compression member in a shorter time than in the related art.

In addition, according to the present embodiment, processing of storing the ultrasound image obtained by scanning using the ultrasound probe and at least one of the scanning region or the scanning direction in the scanning for obtaining the ultrasound image in association with each other is further performed. Accordingly, it is possible to display the ultrasound image corresponding to the position designated for the radiation image.

In addition, according to the present embodiment, at least one of the actual scanning region or the actual scanning direction is specified using the detection result of the position sensor that detects the position of the ultrasound probe. Accordingly, it is not necessary for the user to input at least one of the actual scanning region or the actual scanning direction.

In addition, according to the present embodiment, in a case in which the ultrasound image is stored in association with the scanning region, first display processing of displaying the radiation image corresponding to the ultrasound image together with the scanning region image which is an image showing the scanning region, is further performed, and, in a case in which the scanning region shown in the scanning region image displayed by the first display processing is designated by the user, second display processing of displaying the ultrasound image corresponding to the scanning region is further performed. Accordingly, it is possible to display the ultrasound image corresponding to the radiation image from the radiation image.

In addition, according to the present embodiment, the scanning regions corresponding to scans adjacent to each other are decided such that the adjacent regions overlap each other within a predetermined range. Accordingly, it is possible to more reliably obtain a single ultrasound image as compared with a case in which the overlap is not performed.

In addition, according to the present embodiment, an image including at least one of a line, a figure, a mark, or a character is applied as the guide image. Accordingly, it is possible to project the guide image of the applied type of image.

In addition, according to the present embodiment, the guide image is projected onto the side of the compression member opposite the compression side of the breast and onto the region excluding the scanning region of the ultrasound probe. Accordingly, it is possible to avoid the occurrence of a situation in which the guide image is blocked by the scanning using the ultrasound probe.

In addition, according to the present embodiment, the scanning region is decided by at least one of the width of the housing of the ultrasound probe, the effective width of the ultrasound probe, or the width of the compression member. Accordingly, it is possible to decide the scanning region using the physical quantity that can be acquired in advance.

Further, according to the present embodiment, the effective width is acquired at any one of a timing at which the medical image acquisition guidance device (console 50) is powered on, a timing at which the ultrasound probe is attached, or a timing at which a preset for acquiring an image showing the breast is selected. Accordingly, it is possible to project the guide image at the applied timing.

In the above-described embodiment, a case in which the CPU 51 provided in the console 50 is applied as the processor according to the technique of the present disclosure has been described, but the present disclosure is not limited to this. For example, a form may be adopted in which the CPU of the controller 20 provided in the medical image acquisition apparatus 10 is applied as the processor according to the technology of the present disclosure.

Figure 21:
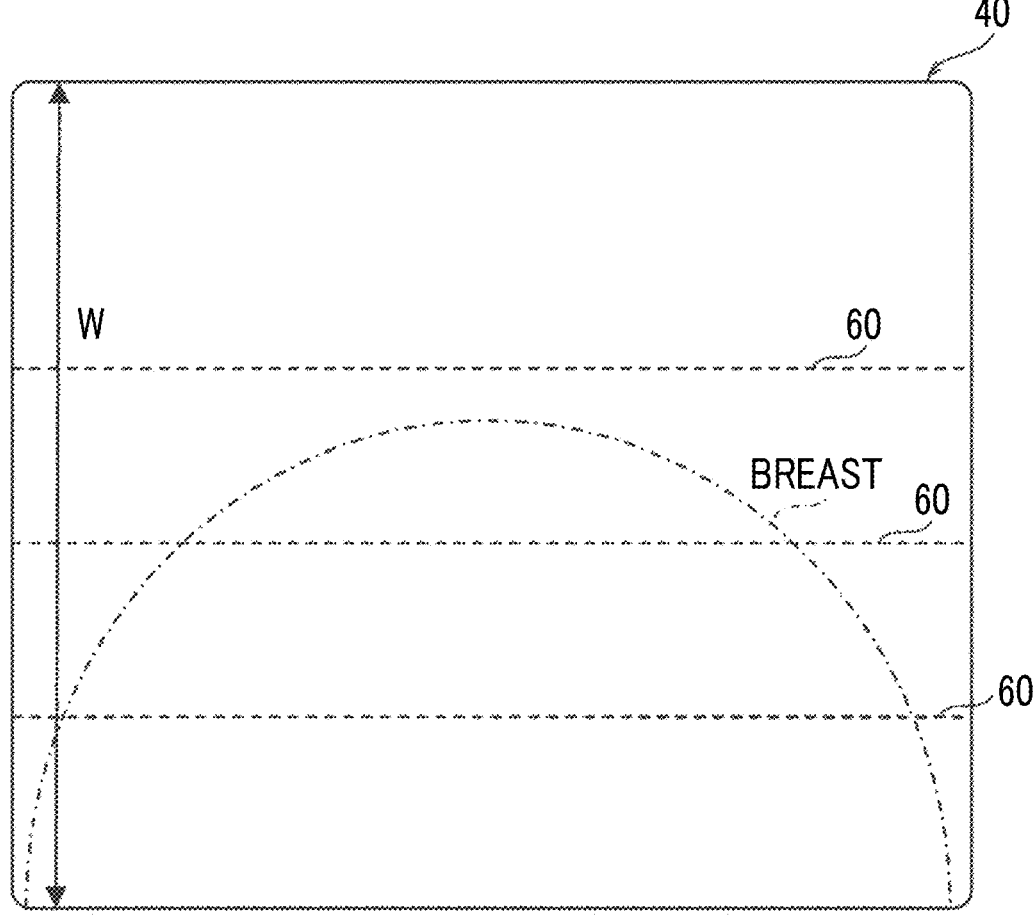
FIG. 21 is a diagram for describing another method of deriving the scanning region and the number of times of scanning according to the embodiment.

In addition, in the above-described embodiment, a case in which the scanning region and the number of times of scanning of the ultrasound probe 30 are decided according to the width W in the depth direction of the upper surface 43A of the bottom portion 43 of the compression member 40 has been described, but the present disclosure is not limited to this. For example, a form may be adopted in which the scanning region and the number of times of scanning of the ultrasound probe 30 are decided according to the region of the breast specified from the radiation image. FIG. 21 is a diagram for describing another method of deriving the scanning region and the number of times of scanning according to the present embodiment.

As shown in FIG. 21, in this case, the scanning region and the number of times of scanning are decided to scan only the region in which the breast exists, instead of scanning the entire region of the width W. In the example shown in FIG. 21, the number of times of scanning is three.

In addition, in the above-described embodiment, a case in which the scanning information is registered in the registration information database 52D has been described, but the present disclosure is not limited to this. For example, a form may be adopted in which the scanning information is registered in a private tag of an image defined by digital imaging and communications in medicine (DICOM), which is a common standard for medical images.

In addition, in the above-described embodiment, for example, as a hardware structure of processing units that execute various types of processing, such as the probe information acquisition unit 51A, the scanning information derivation unit 51B, the guide image creation unit 51C, the projection processing unit 51D, the specifying unit 51E, the storage processing unit 51F, the first display processing unit 51G, and the second display processing unit 51H, various processors shown below can be used. The various processors include, as described above, in addition to a CPU, which is a general-purpose processor that functions as various processing units by executing software (program), a programmable logic device (PLD) that is a processor of which a circuit configuration may be changed after manufacture, such as a field programmable gate array (FPGA), and a dedicated electrical circuit which is a processor having a circuit configuration specially designed to execute specific processing, such as an application specific integrated circuit (ASIC).

One processing unit may be configured of one of the various processors, or may be configured of a combination of the same or different kinds of two or more processors (for example, a combination of a plurality of FPGAs or a combination of the CPU and the FPGA). In addition, a plurality of processing units may be configured of one processor.

As an example in which a plurality of processing units are configured of one processor, first, as typified by a computer such as a client or a server, there is an aspect in which one processor is configured of a combination of one or more CPUs and software, and this processor functions as a plurality of processing units. Second, as typified by a system on chip (SoC) or the like, there is an aspect in which a processor that implements functions of the entire system including the plurality of processing units via one integrated circuit (IC) chip is used. As described above, various processing units are configured by using one or more of the various processors as a hardware structure.

Further, as the hardware structure of the various processors, more specifically, an electric circuit (circuitry) in which circuit elements such as semiconductor elements are combined may be used.

In addition, in the above-described embodiment, a form in which each program of the projection processing program 52A and the image display processing program 52B is stored (installed) in advance in the storage unit 52 of the console 50 has been described, but the present disclosure is not limited to this. Each program may be provided in a form of being recorded on a recording medium such as a compact disc read only memory (CD-ROM), a digital versatile disc read only memory (DVD-ROM), or a universal serial bus (USB) memory. In addition, a form may be adopted in which each program is downloaded from an external device via the network.

From the above description, the invention described in following Appendices can be understood.

Appendix 1

A medical image acquisition guidance device comprising:
at least one processor,
in which the processor is configured to, in a case in which a radiation image and an ultrasound image of a breast in a state of being compressed by a compression member are captured, perform processing of projecting a guide image for guiding at least one of a scanning region or a scanning direction of an ultrasound probe used for capturing the ultrasound image onto a side of the compression member opposite to a compression side of the breast according to an effective width, which is a region in which transmission and reception of an ultrasonic wave are possible, of the ultrasound probe, in capturing the ultrasound image.

Appendix 2

The medical image acquisition guidance device according to Appendix 1,
in which the processor is configured to further perform processing of storing the ultrasound image obtained by scanning using the ultrasound probe and at least one of the scanning region or the scanning direction in the scanning for obtaining the ultrasound image in association with each other.

Appendix 3

The medical image acquisition guidance device according to Appendix 2, in which the processor is configured to specify at least one of an actual scanning region or an actual scanning direction using a detection result of a position sensor that detects a position of the ultrasound probe.

Appendix 4

The medical image acquisition guidance device according to Appendix 2 or 3, in which the processor is configured to in a case in which the ultrasound image is stored in association with the scanning region, further perform first display processing of displaying the radiation image corresponding to the ultrasound image together with a scanning region image which is an image showing the scanning region, and in a case in which the scanning region shown in the scanning region image displayed by the first display processing is designated by a user, further perform second display processing of displaying the ultrasound image corresponding to the scanning region.

Appendix 5

The medical image acquisition guidance device according to any one of Appendices 1 to 4, in which the processor is configured to, in a case in which scanning using the ultrasound probe is performed a plurality of times to capture a single ultrasound image, decide the scanning regions corresponding to scans adjacent to each other such that the adjacent regions overlap each other within a predetermined range.

Appendix 6

The medical image acquisition guidance device according to any one of Appendices 1 to 5, in which the guide image is an image including at least one of a line, a figure, a mark, or a character.

Appendix 7

The medical image acquisition guidance device according to any one of Appendices 1 to 6, in which the processor is configured to project the guide image onto the side of the compression member opposite to the compression side of the breast and onto a region excluding the scanning region of the ultrasound probe.

Appendix 8

The medical image acquisition guidance device according to any one of Appendices 1 to 7, in which the processor is configured to decide the scanning region using at least one of a width of a housing of the ultrasound probe, the effective width of the ultrasound probe, a width of the compression member, or an acquisition region of an image showing the breast in the radiation image.

Appendix 9

The medical image acquisition guidance device according to any one of Appendices 1 to 8, in which the processor is configured to acquire the effective width at any one of a timing at which the medical image acquisition guidance device is powered on, a timing at which the ultrasound probe is attached, or a timing at which a preset for acquiring an image showing the breast is selected.

Appendix 10

A medical image acquisition guidance system comprising:

the medical image acquisition guidance device according to any one of Appendices 1 to 9; and a display unit that displays the radiation image and the ultrasound image acquired in accordance with the processing performed by the medical image acquisition guidance device.

Appendix 11

A program causing a computer to execute a process comprising:

performing, in a case in which a radiation image and an ultrasound image of a breast in a state of being compressed by a compression member are captured, processing of projecting a guide image for guiding at least one of a scanning region or a scanning direction of an ultrasound probe used for capturing the ultrasound image onto a side of the compression member opposite to a compression side of the breast according to an effective width, which is a region in which transmission and reception of an ultrasonic wave are possible, of the ultrasound probe, in capturing the ultrasound image.

What is claimed is:

1. A medical image acquisition guidance device comprising:

a processor; and a projection unit, wherein the processor is configured to, in a case in which a radiation image and an ultrasound image of a breast in a state of being compressed by a compression member are captured, in capturing the ultrasound image, generate a guide image for guiding at least one of a scanning region or a scanning direction of an ultrasound probe used for capturing the ultrasound image according to an effective width, which is a region in which transmission and reception of an ultrasonic wave are possible, of the ultrasound probe, and perform projection processing of causing the guide image to be projected onto an opposite side of the compression member from a compression side of the breast by controlling the projection unit.

2. The medical image acquisition guidance device according to claim 1, wherein the processor is configured to further perform processing of storing the ultrasound image obtained by scanning using the ultrasound probe and at least one of the scanning region or the scanning direction in the scanning for obtaining the ultrasound image in association with each other.

3. The medical image acquisition guidance device according to claim 2, wherein the processor is configured to specify at least one of an actual scanning region or an actual scanning direction using a detection result of a position sensor that detects a position of the ultrasound probe.

4. The medical image acquisition guidance device according to claim 2, wherein the processor is configured to in a case in which the ultrasound image is stored in association with the scanning region, further perform first display processing of displaying the radiation image corresponding to the ultrasound image together with a scanning region image which is an image showing the scanning region, and in a case in which the scanning region shown in the scanning region image displayed by the first display processing is designated by a user, further perform second display processing of displaying the ultrasound image corresponding to the scanning region.

5. The medical image acquisition guidance device according to claim 1, wherein the processor is configured to, in a case in which scanning using the ultrasound probe is performed a plurality of times to capture a single ultrasound image, decide the scanning regions corresponding to scans adjacent to each other such that the adjacent regions overlap each other within a predetermined range.

6. The medical image acquisition guidance device according to claim 1, wherein the guide image is an image including at least one of a line, a figure, a mark, or a character.

7. The medical image acquisition guidance device according to claim 1, wherein the processor is configured to control the projection unit so as to project the guide image onto the opposite side of the compression member from the compression side of the breast and onto a region excluding the scanning region of the ultrasound probe.

8. The medical image acquisition guidance device according to claim 1, wherein the processor is configured to decide the scanning region using at least one of a width of a housing of the ultrasound probe, the effective width of the ultrasound probe, a width of the compression member, or an acquisition region of an image showing the breast in the radiation image.

9. The medical image acquisition guidance device according to claim 1, wherein the processor is configured to acquire the effective width at any one of a timing at which the medical image acquisition guidance device is powered on, a timing at which the ultrasound probe is attached, or a timing at which a preset for acquiring an image showing the breast is selected.

10. A medical image acquisition guidance system comprising:

the medical image acquisition guidance device according to claim 1; and a display that displays the radiation image and the ultrasound image acquired in accordance with the processing performed by the medical image acquisition guidance device.

11. A non-transitory computer-readable storage medium storing a program executable by a computer to execute a process comprising:

performing, in a case in which a radiation image and an ultrasound image of a breast in a state of being compressed by a compression member are captured, in capturing the ultrasound image, generate a guide image for guiding at least one of a scanning region or a scanning direction of an ultrasound probe used for capturing the ultrasound image according to an effective width, which is a region in which transmission and reception of an ultrasonic wave are possible, of the ultrasound probe, and perform projection processing of causing the guide image to be projected onto an opposite side of the compression member from a compression side of the breast by controlling a projection unit.

* * * * *